(12) United States Patent
Bush, Jr. et al.

(10) Patent No.: US 7,776,018 B2
(45) Date of Patent: Aug. 17, 2010

(54) LUER CONNECTOR ASSEMBLY

(75) Inventors: Charles L. Bush, Jr., Fairfield, NJ (US); Gene Fleischer, New City, NY (US); Charles G. Hwang, Ridgewood, NJ (US); C. Mark Newby, Tuxedo, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 11/875,178

(22) Filed: Oct. 19, 2007

(65) Prior Publication Data
US 2008/0039800 A1 Feb. 14, 2008

Related U.S. Application Data

(62) Division of application No. 10/485,082, filed as application No. PCT/US02/15888 on May 21, 2002, now abandoned.

(60) Provisional application No. 60/308,380, filed on Jul. 27, 2001.

(51) Int. Cl.
*A61M 5/31* (2006.01)
*A61M 25/18* (2006.01)
*F16L 19/00* (2006.01)

(52) U.S. Cl. ................. 604/243; 604/240; 604/535; 285/345

(58) Field of Classification Search ......... 604/533–539, 604/240–3, 202, 237, 215; 285/345, 334.1, 285/332.4, 332.2, 332.1, 332
See application file for complete search history.

(56) References Cited

U.S. PATENT DOCUMENTS 1,873,304 A * 8/1932 De Mooy ............... 285/277

| | | |
|---|---|---|
| 2,711,171 A | 6/1955 | Dunnican |
| 2,764,978 A * | 10/1956 | Everett ............... 604/242 |
| 2,902,995 A | 9/1959 | Loper |
| 3,402,713 A | 9/1968 | Senkowski et al. |
| 3,524,445 A | 8/1970 | Frieze |
| 4,040,421 A | 8/1977 | Young |
| 4,187,848 A | 2/1980 | Taylor |

(Continued)

OTHER PUBLICATIONS

Advanced Elastomer Systems, Santoprene Thermoplastic Rubber, 2001, pp. 1-19.

(Continued)

*Primary Examiner*—Kevin C Sirmons
*Assistant Examiner*—Catherine N Witczak
(74) *Attorney, Agent, or Firm*—Diehl Servilla LLC

(57) ABSTRACT

A luer connector assembly is provided for enhancing the frictional engagement between medical devices such as syringes and needle assemblies. The assembly needle includes a female luer fitting having a passageway and a relatively soft, resilient member bounding the passageway. The passageway is also bounded by the body of the fitting, which is harder than the soft, resilient member. A male luer fitting inserted into the passageway engages both the soft, resilient member and the body of the female luer fitting. A method of manufacturing such a connector assembly is further provided. A first material is injected into a mold to form the body of a female luer fitting, the fitting including a passageway and a recess extending into the body. A second material is then injected such that it extends into the recess and bounds the passageway. The second material, when cool, is softer than the first material.

11 Claims, 28 Drawing Sheets

U.S. PATENT DOCUMENTS

| | | | |
|---|---|---|---|
| 4,369,781 | A | 1/1983 | Gilson et al. |
| 4,589,871 | A | 5/1986 | Imbert |
| 4,613,329 | A | 9/1986 | Bodicky |
| 4,676,530 | A | 6/1987 | Nordgren et al. |
| 4,935,010 | A * | 6/1990 | Cox et al. ................... 604/122 |
| 4,982,842 | A | 1/1991 | Hollister |
| 5,290,246 | A * | 3/1994 | Yamamoto et al. ..... 604/167.03 |
| 5,312,377 | A | 5/1994 | Dalton |
| 5,336,192 | A * | 8/1994 | Palestrant .............. 604/167.04 |
| 5,851,201 | A | 12/1998 | Ritger et al. |
| 5,964,737 | A | 10/1999 | Caizza |
| 6,217,560 | B1 | 4/2001 | Ritger et al. |
| 6,325,782 | B1 | 12/2001 | Lopez |
| 6,569,125 | B2 | 5/2003 | Jepson |
| 6,869,418 | B2 | 3/2005 | Marano-Ford |
| 2002/0010425 | A1 | 1/2002 | Guo et al. |
| 2002/0053800 | A1 * | 5/2002 | Seifert et al. ................ 285/341 |
| 2005/0065481 | A1 | 3/2005 | Hauri et al. |
| 2005/0065482 | A1 | 3/2005 | Hauri et al. |

OTHER PUBLICATIONS

Advanced Elastomer Systems, Medical Grades of Santoprene Thermoplastic Rubber, 2001, pp. 1-37.

IDES, Santoprene Rubber 281-55, 2002, http://prwebf.ides.com/datasheet.asp?varAAA=796.

IDES, Santoprene Rubber 171-55, 2002, http://prwebf.ides.com/datasheet.asp?varAAA-24464.

Non-Final Office Action in U.S. Appl. No. 12/170,684, (Nov. 12, 2009), 9 pgs.

Final Office Action in U.S. Appl. No. 12/170,684, mailed Feb. 24, 2010, 11 pp.

* cited by examiner

LUER CONNECTOR ASSEMBLY

RELATED APPLICATIONS

This application is a divisional application of U.S. Serial application Ser. No. 10/485,082 filed Jan. 26, 2004, which is a 371 of Application No. PCT/US02/15888 filed May 21, 2002, which claims the benefit of U.S. Application Ser. No. 60/308,380 filed Jul. 27, 2001, now abandoned.

BACKGROUND OF THE INVENTION

1. Field of the Invention

The field of the invention relates to luer connector assemblies, and methods for manufacturing such assemblies.

2. Brief Description of the Prior Art

Generally speaking, a hypodermic syringe consists of a cylindrical barrel, most commonly made of thermoplastic material or glass, with a distal end adapted to be connected to a hypodermic needle and a proximal end adapted to receive a stopper and plunger rod assembly. One of the purposes of the stopper is to provide a relatively air tight seal between itself and the syringe barrel so that movement of the stopper up and down the barrel will cause fluids to be drawn into or forced out of the syringe through the distal end. The stopper is moved along the syringe barrel by applying axial force on a rigid plunger rod which is connected to the stopper and is sufficiently long to be accessible outside of the barrel.

Hypodermic needle assemblies, typically including a cannula and a hub, are often times removably attached to syringes for performing a variety of tasks such as the delivery of medication into patients and into devices, and for withdrawing fluid samples from patients and from fluid sources. Usually, the hub of the hypodermic needle assembly has a tapered interior surface adapted to engage the tapered tip of the syringe barrel so that the two components are joined in a frictional interference fit. The tapered syringe tip and the complementary tapered receptacle in the hub are referred to as standard luer fittings. A wide variety of other devices such as stopcocks and tubing sets have standard luer fittings which allow them to be engaged to a syringe tip.

It is important that the frictional fit between the syringe tip and the needle hub or other device is strong enough to prevent accidental disengagement caused by the fluid pressures within the syringe and/or other factors. If the syringe tip becomes disengaged from the other fluid delivery means, medications, blood or other fluids will be lost and there is also potential for contamination of the fluid.

To improve the strength of the interference fit between the syringe tip and the fluid delivery device, such as a hypodermic needle, many prior art devices, such as a hypodermic syringe, provide a circular internally threaded receptacle which is concentric to and larger than the luer tip of the syringe barrel. The hypodermic needle or other fitting used with this type of syringe has wings projecting radially outwardly from the base of the needle hub so that the needle hub may be placed on the syringe tip and rotated in a clockwise direction until the hub wings engage the threads at the syringe tip and pull the needle hub into tight frictional engagement with the syringe tip. This type of fitting is commonly referred to as a luer lock. With a plastic syringe barrel the threaded luer lock collar can be molded integrally with the syringe barrel as taught in U.S. Pat. No. 3,402,713 to Senkowski et al. When using a glass syringe barrel the threaded collar is usually made of a relatively expensive metal part which is chrome plated and attached to the glass syringe. Such a device is taught in U.S. Pat. No. 2,711,171 to Dunnican. The type of device taught by Dunnican is commonly found on reusable glass syringes. However, its relative expense makes it impractical for a disposable syringe assembly.

It is known to blast the tip of a glass syringe with abrasive particles, such as aluminum oxide beads or sand, to increase the roughness of the tip and, therefore, the strength of the frictional interference fit between the syringe tip and the needle hub. The roughened surface also is believed to be helpful in the event that liquid is accidentally deposited on the syringe tip, because the roughened surface is better able to break through the liquid film as the needle hub is engaged thereon. A disadvantage of abrasive blasting a syringe tip to obtain a roughened surface is that the debris created by the blasting process must be thoroughly and completely removed from the syringe barrel. This cleanup operation is an expensive secondary operation which is required because of the medical uses most syringes are placed in.

U.S. Pat. No. 5,312,377 discloses male and female luer members that are comprised of soft, resilient, elastomeric materials. When coupled, the outer periphery of the female luer member conforms to the threads of the luer lock collar of the male luer member. Stiffening inserts may be encapsulated within the luer members using a process referred to as insert molding.

The syringe tip may alternatively be coated, as disclosed in U.S. Pat. No. 4,589,871 to increase the roughness of the syringe tip. Texturing of the male and female portions of the luer connector to improve retention is disclosed in U.S. Pat. Nos. 5,851,201 and 6,217,560 B1.

Various mechanical locking features have been proposed for coupling syringe tips and needle hubs. U.S. Pat. Nos. 2,764,978 and 2,902,995 disclose examples of such locking or detent features. U.S. Pat. No. 4,040,421 discloses a needle hub having an internal bead that forms a depression in a boss surface on the syringe, thereby supplementing the interference fit. U.S. Pat. Nos. 4,369,781 and 4,676,530 disclose locking members such as lock washers used to enhance the retention of male and female luer fittings.

SUMMARY OF THE INVENTION

The present invention provides a luer connector assembly that can be used to reliably couple a needle hub with a syringe, or to couple other medical devices having luer slip connector portions or fittings. A material is provided within a recess in a hub that will enhance the frictional interference fit between the hub and the medical device to which it is connected. In accordance with a preferred embodiment of the invention, a relatively soft, resilient material is used to form an engagement surface, and is provided within a relatively rigid fitting. As the tip of a medical device is mated to the fitting, the relatively soft material is compressed, thereby providing a more secure connection than would ordinarily be achieved by an interference fit between two fittings made solely from rigid or semi-rigid materials. The soft, resilient material can, for example, be incorporated in the fitting using a two shot molding process where the fitting is first molded and the relatively soft material is then molded on the fitting.

A needle assembly is provided in accordance with an embodiment of the invention that reduces the chance of accidental disengagement from a medical device such as a syringe. The assembly includes a female luer fitting having a relatively rigid body including a proximal end, a distal end, a tapered interior surface and an outer surface. A passageway extends through the body between the proximal and distal ends. A cannula is connected to the distal end of the body of the fitting. The cannula is in fluid communication with the passageway. A soft, resilient member is secured to the body of the fitting and bounds the passageway. This member frictionally retains a male luer member once inserted into the passageway. The soft, resilient member bounds only a portion of the passageway such that the male luer member engages both the relatively rigid body of the female luer fitting as well as the relatively soft, resilient member.

An assembly for transferring fluid from a first medical device to a second medical device is also provided. The first medical device includes a male luer fitting having a tapered exterior surface. The second medical device includes a female luer fitting having a relatively rigid or semi-rigid body and a tapered interior surface. The male and female fittings are coupled such that the tapered exterior surface of the male luer fitting adjoins the tapered interior surface of the female luer fitting. The female luer fitting includes a passageway bounded by the tapered interior surface. A relatively soft, resilient member is secured to the body of the female luer fitting and bounds the passageway. The resilient member is deformed by the exterior surface of the male luer fitting, thereby increasing the reliability of the connection of the male and female luer fittings. The male luer fitting preferably engages both the soft, resilient member and the body of the female luer fitting.

A method of manufacturing a luer fitting to provide enhanced frictional surface(s) is further provided. The method includes the multi-shot molding of the fitting wherein two materials are employed, one to form the body of the fitting and the other to form at least part of a relatively soft inner surface thereof. In accordance with the method, a first material is injected into the mold to form the body of a female luer fitting having an interior surface including a recess. A second material, which when cool is softer than the first material, is then injected such that it is positioned in the recess in the interior surface of the female luer fitting and is coupled to the body of the fitting.

DETAILED DESCRIPTION OF THE INVENTION

Figure 1:
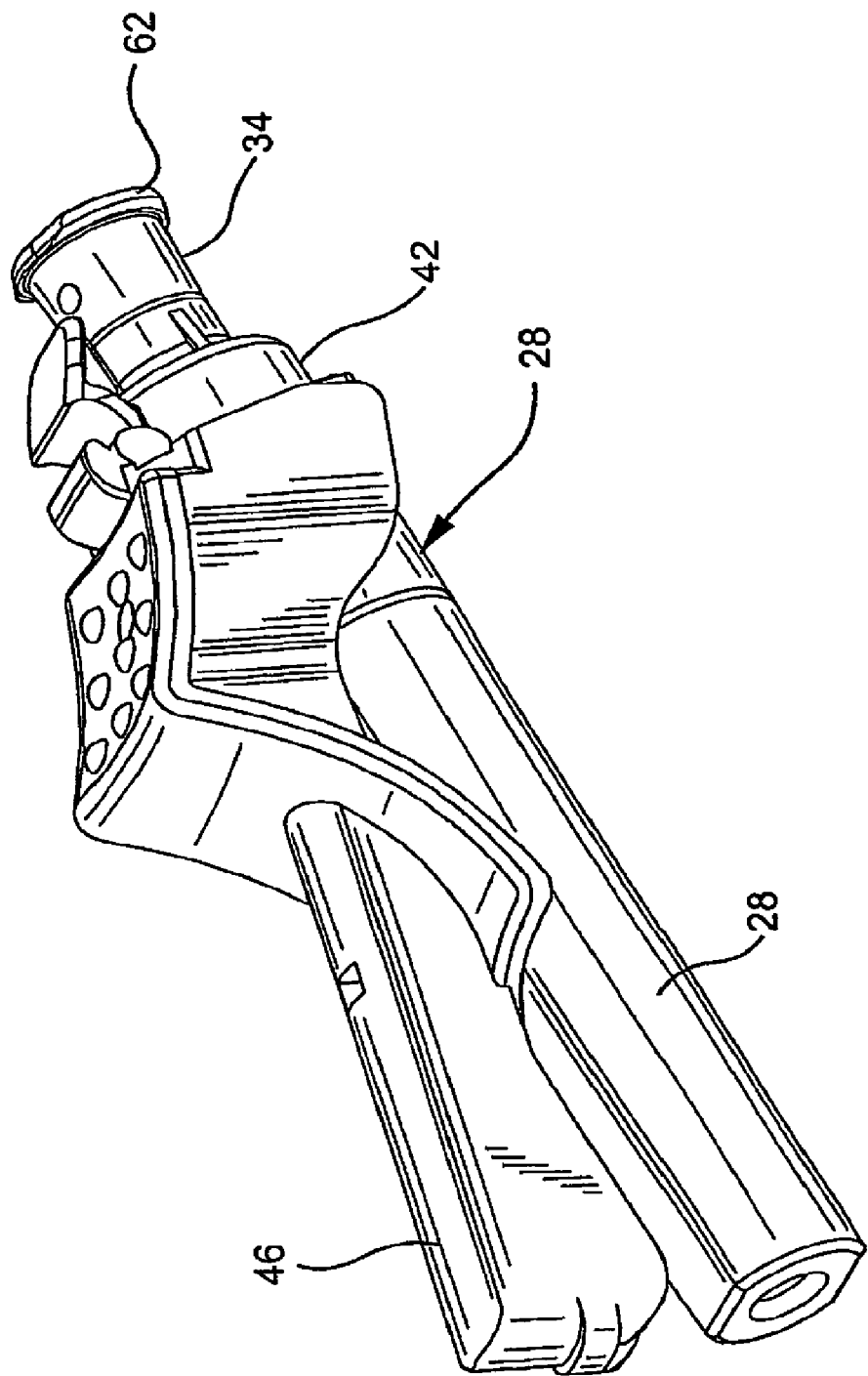
FIG. 1 is a top perspective view of a syringe and needle assembly including a needle shield and sheath in accordance with the invention.

There is shown in the drawings and described below in detail preferred embodiments of the invention with the understanding that the present disclosure is to be considered as exemplary of the principles of the invention and is not intended to limit the invention to the embodiments illustrated.

Figure 2:
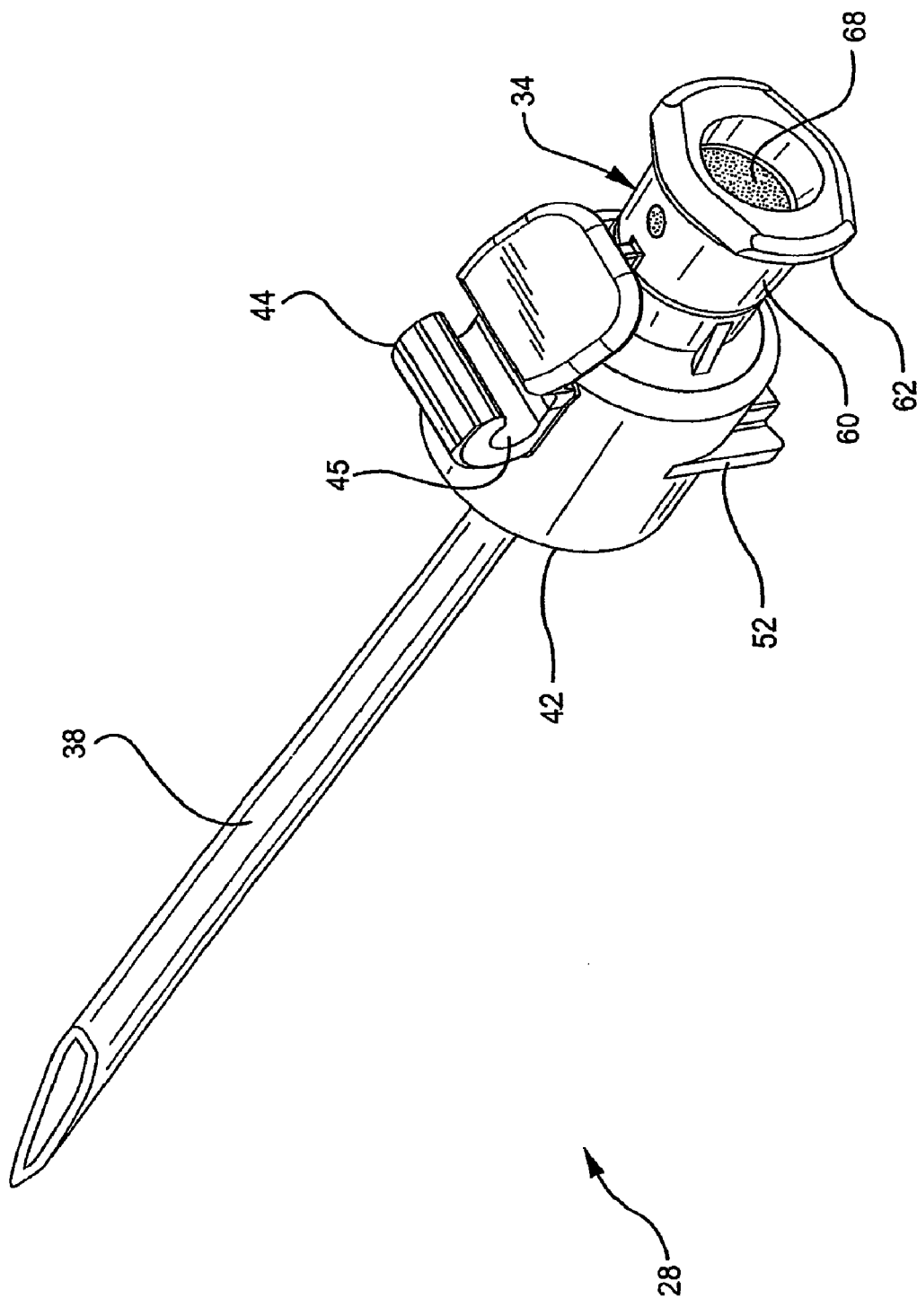
FIG. 2 is a perspective view of a needle assembly in accordance with the invention.
Figure 3:
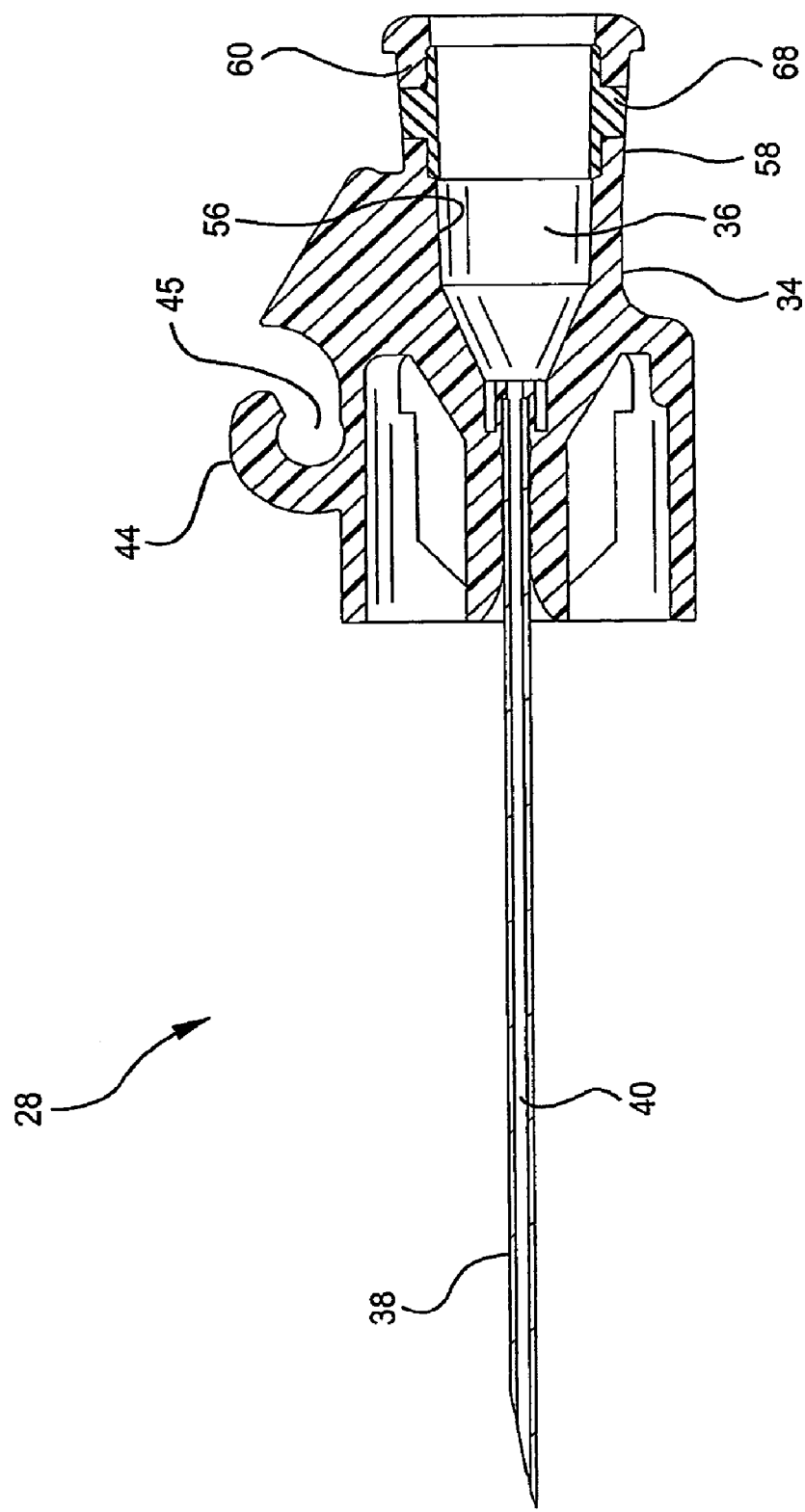
FIG. 3 is a cross-sectional view of the needle assembly of FIG. 2.
Figure 4:
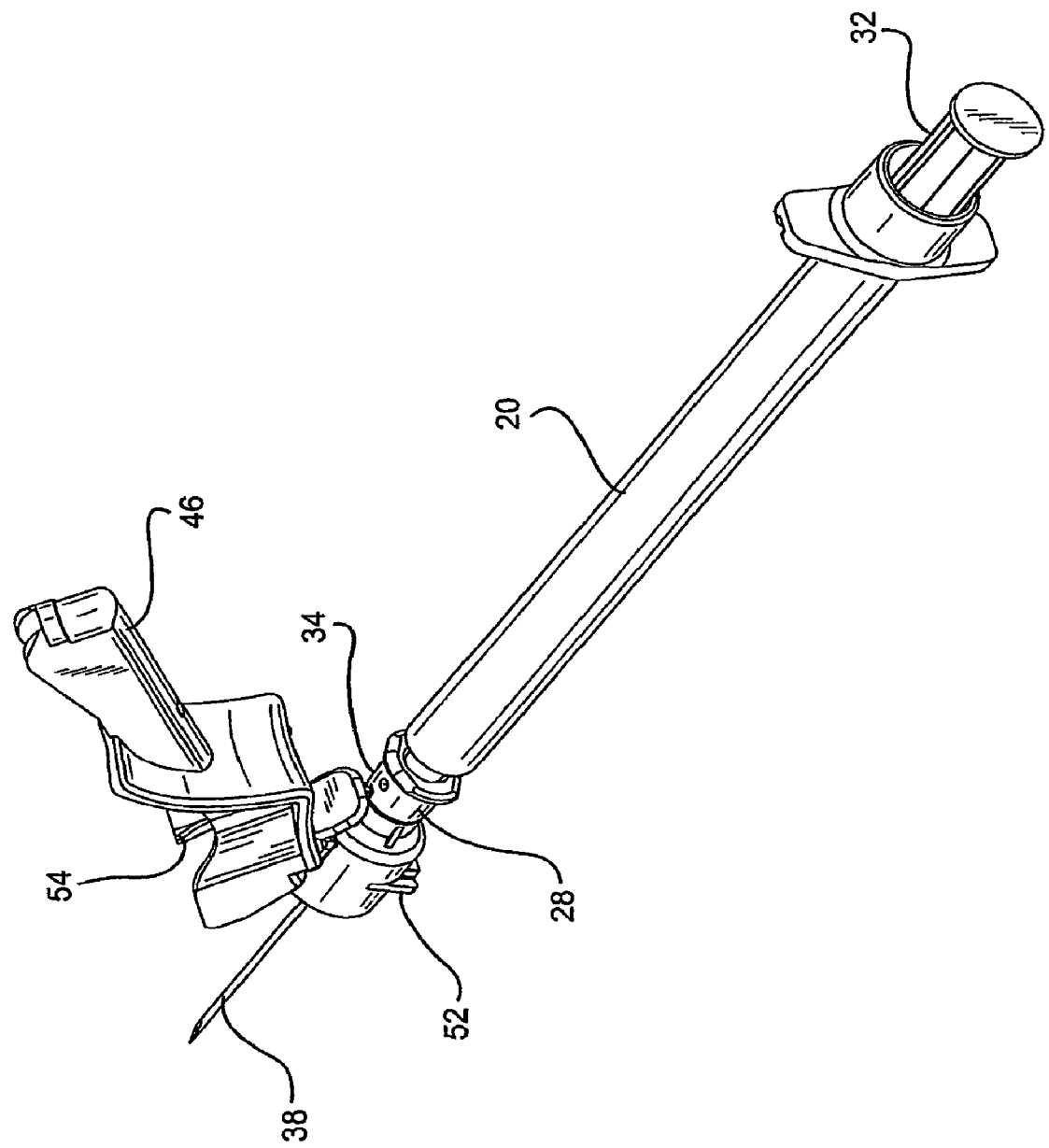
FIG. 4 is a top perspective view showing the needle assembly with a needle shield, coupled to a syringe, the needle shield being in the open position.
Figure 5:
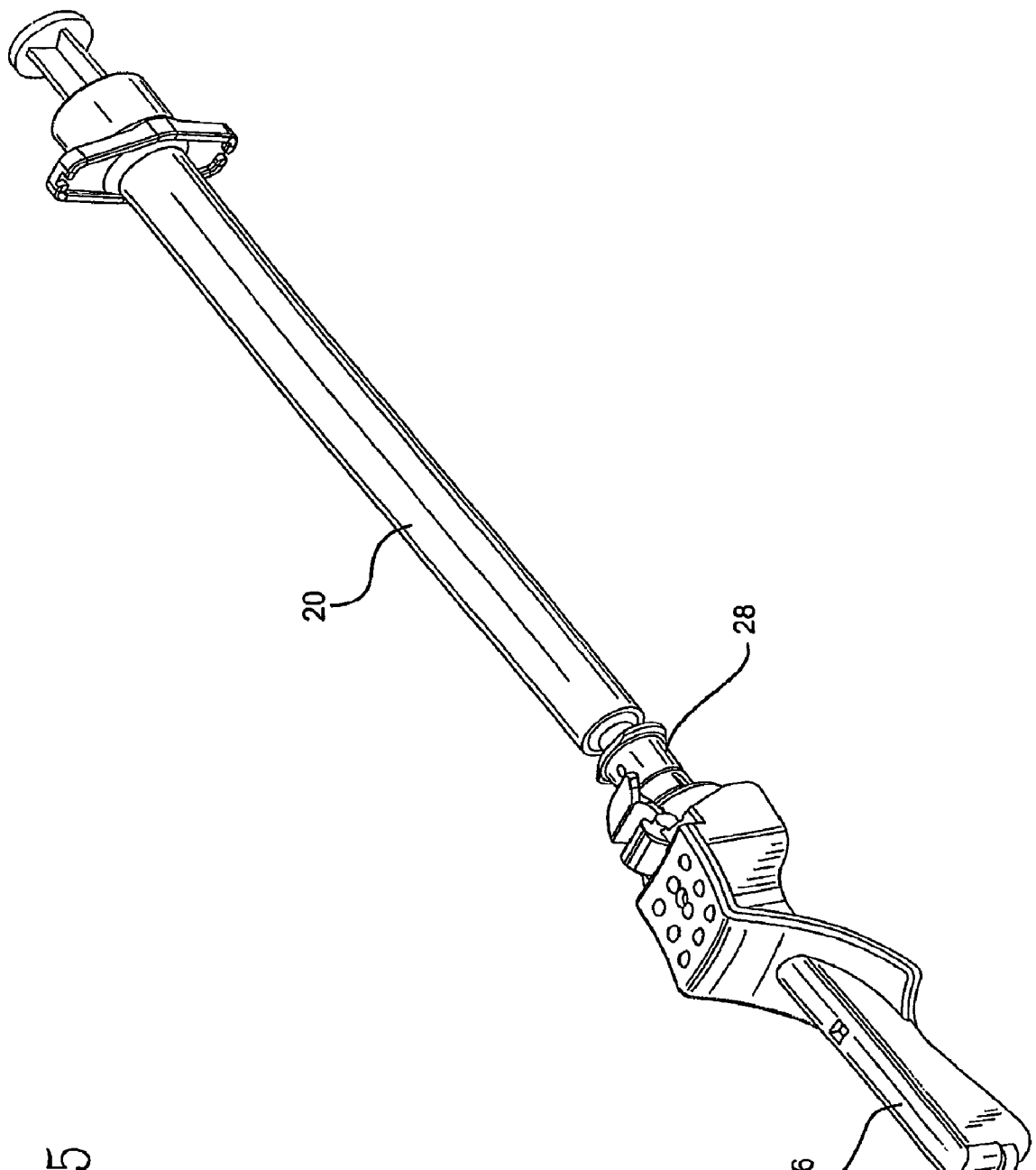
FIG. 5 is a top perspective view thereof showing the needle shield in the closed position.
Figure 6:
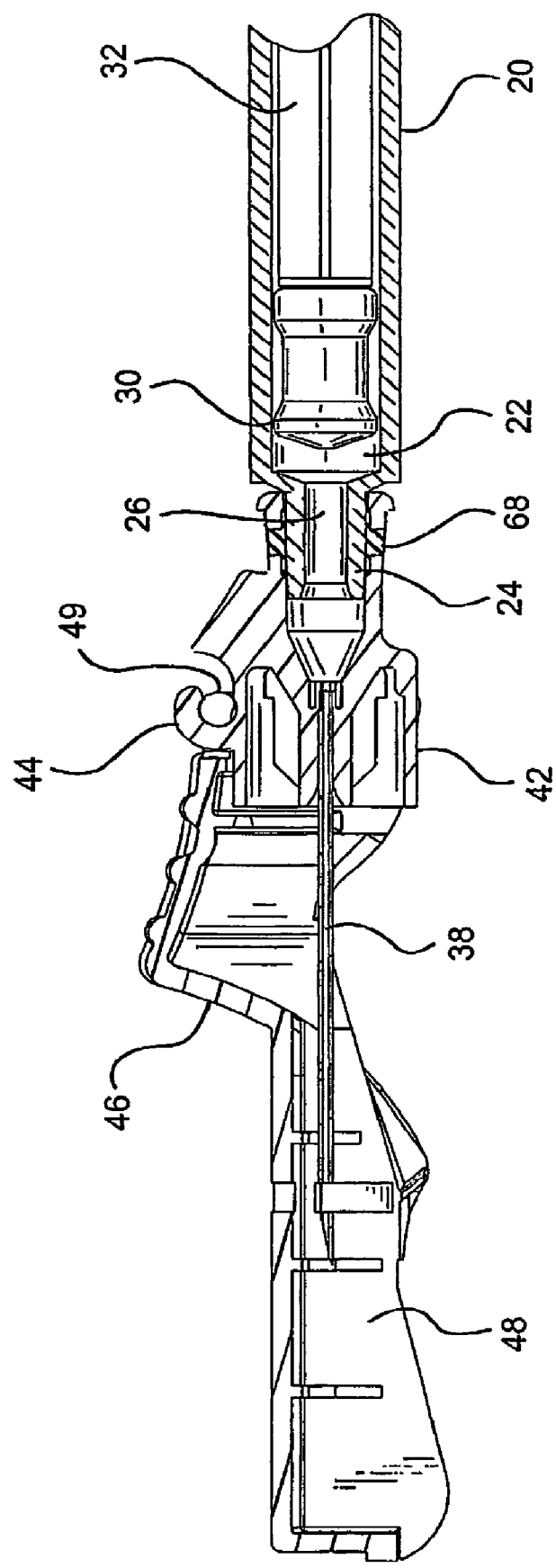
FIG. 6 is a cross-sectional view of the needle assembly with a needle shield.

A first embodiment of the invention will be described with respect to FIGS. 1-10. FIGS. 1-3 show a hypodermic needle assembly 28 according to the invention, while FIGS. 4-6 show the assembly as coupled to a syringe. The syringe includes a barrel 20 that comprises an elongate chamber 22 for retaining fluids. A tip 24 extends from the distal end of the barrel. The tip 24 includes a passageway 26 for communicating with the chamber 22, as shown in FIG. 6. The tip 24 is used to connect the syringe to the hypodermic needle assembly 28, though it could also be used to engage other fluid transfer apparatus. It will further be appreciated that the present invention is applicable to the engagement of other types of medical devices having connector assemblies comprised of tips and hub portions mounted over the tips. Some evacuated tube holders, for example, have tips for accepting needle assemblies or tubing.

The syringe tip 24 is preferably frusto-conically shaped, having a smaller outside diameter at its distal end than at its proximal end. It is often referred to as a luer tip or male luer fitting. Such tips are ordinarily tapered in accordance with trade standards to allow the coupling of parts made by different manufacturers.

The syringe barrel may be used in a hypodermic syringe assembly which includes the syringe barrel 20, the hypodermic needle assembly 28, a preferably resilient stopper 30 and a plunger rod 32. The stopper is slidably positioned in fluid-tight engagement inside the barrel 20. The stopper is connected to the plunger rod 32. The plunger rod is accessible outside of the proximal end of the syringe barrel and is provided to move the stopper along the barrel to force fluid into or out of chamber 22 through the passageway 26. Specifically, the stopper is capable of moving fluid from the chamber through the passageway upon its movement toward the distal end of the barrel, and is capable of facilitating the drawing of fluid into the chamber through the tip passageway upon its movement away from the distal end of the barrel. One-piece plunger rod/stopper assemblies can also be used.

The hypodermic needle assembly 28, as best shown in FIG. 3, includes a hub 34 having a proximal end, a distal end, and a passageway 36 therethrough. A cannula 38 having a lumen 40 therethrough is connected to the distal end of the hub preferably using an adhesive such as epoxy so that the lumen of the cannula is in fluid communication with the passageway 36 of the hub. The cannula in this embodiment includes a sharpened distal tip adapted to pierce a patient's flesh or other cutting configurations for the purpose of transferring fluid. Accordingly, movement of the stopper towards the distal end of syringe barrel 20 causes fluid to flow from the barrel through passageway 26 in the barrel, through the hub passageway 36 and through the lumen of the cannula. Cannulas having blunt tips are also well known, and within the purview of the present invention. Such cannulas are often used in connection with injection sites having preslit septums. One-piece hub and cannula assemblies are known to the art, and could be employed in accordance with the invention.

Figure 7:
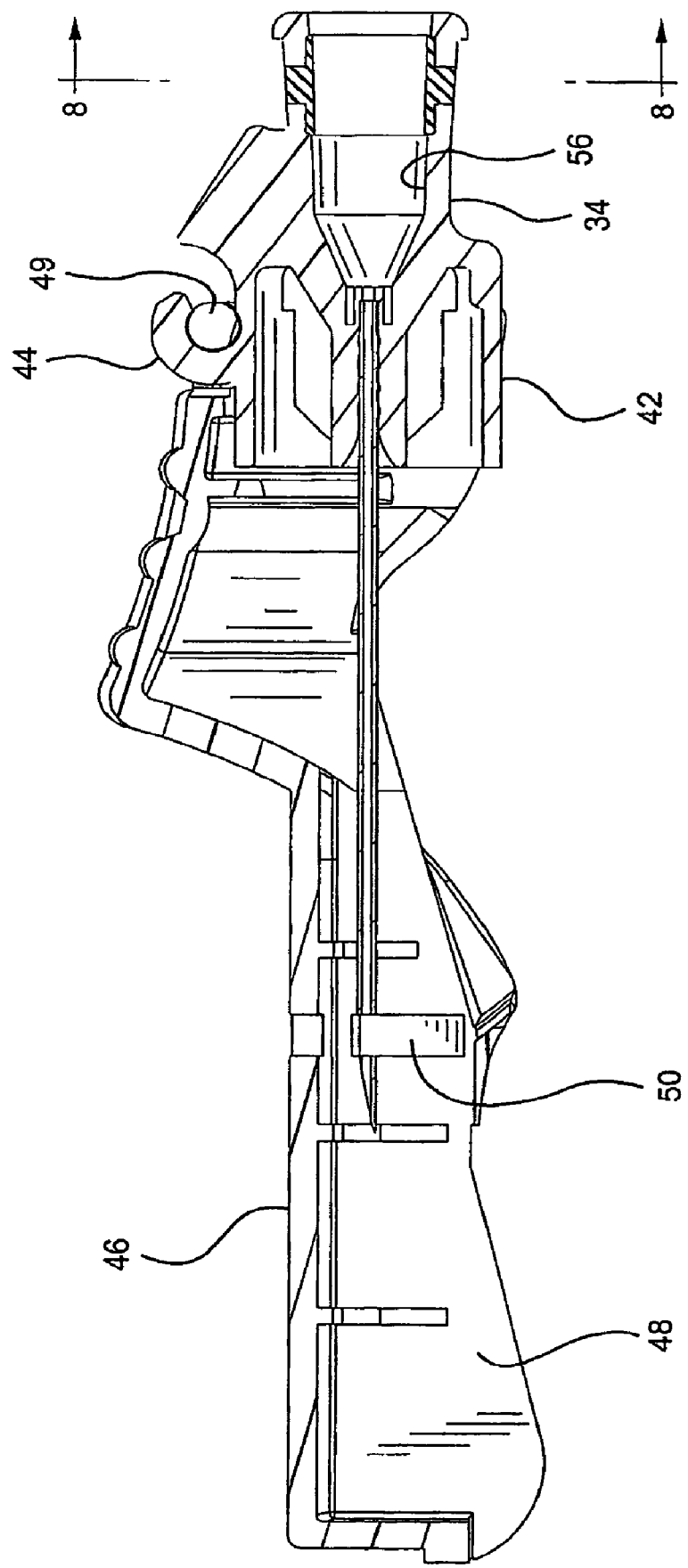
FIG. 7 is an enlarged cross-sectional view showing the needle assembly and the shield in the closed position.
Figure 8:
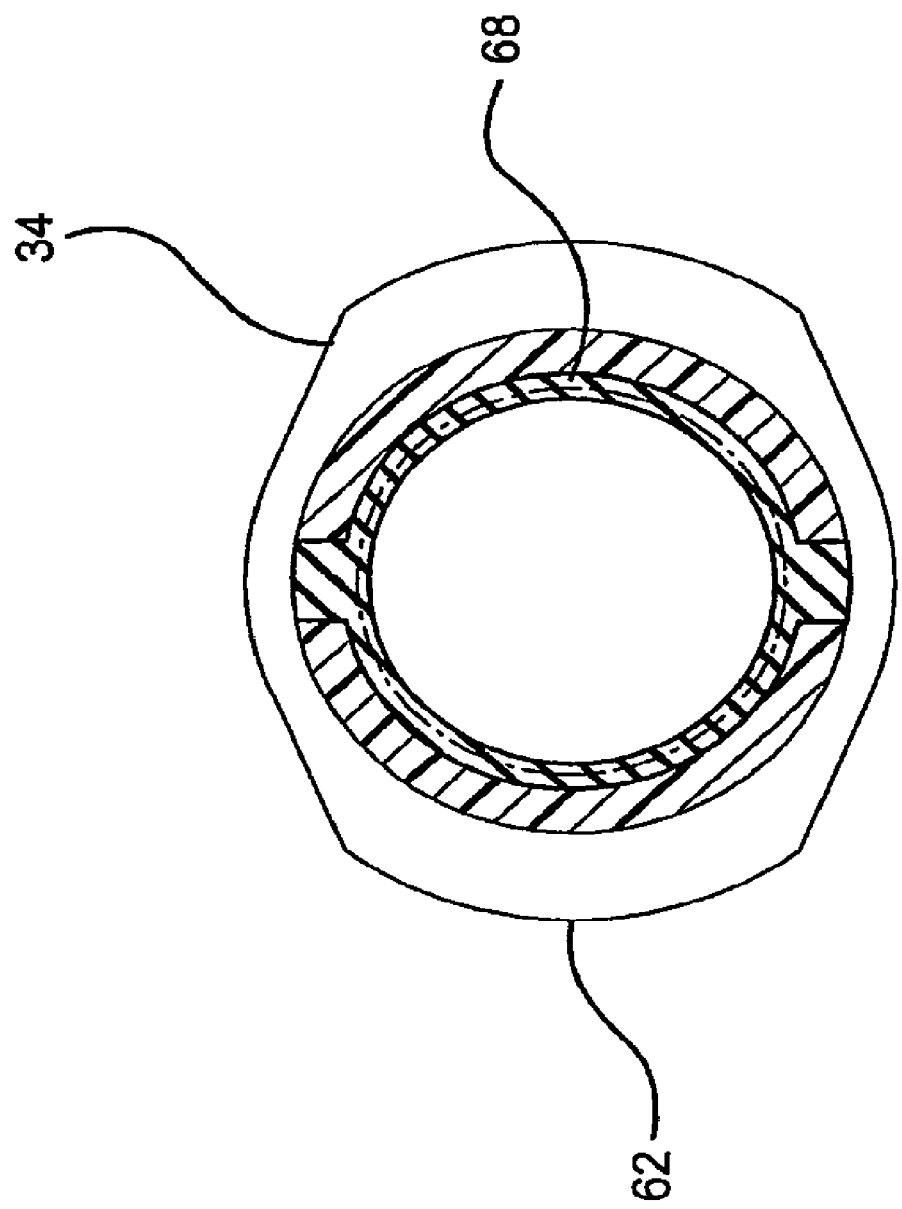
FIG. 8 is a cross-sectional view taken along line 8-8 of FIG. 7.

This embodiment, preferably includes a housing 42 which is desirably integral with hub 34. The housing includes a generally cylindrical body having an open distal end that surrounds the distal end of the needle hub. A hook-like projection 44 extends from the housing and defines a channel 45 that can be used to secure a pivotable needle shield 46. The needle shield includes a cavity 48 for covering the cannula 38. A pivot pin 49 on the needle shield pivotably couples it to the channel 45. FIGS. 6-7 show this coupling. The needle shield may also be pivotably connected to the female luer fitting either directly or indirectly through the housing a living hinge or mechanical hinge or linkage structure suitable for providing pivotable rotation of the needle shield. The needle shield is capable of rotating from an open position wherein said cannula is exposed to a closed cannula protecting position wherein at least a distal portion of the cannula is in the cavity. One or more deflectable projections 50 extend from the sidewall of the shield 46 into the cavity. As shown in FIGS. 6-7, the cannula 38 is trapped within the cavity by the projections 50 when the needle shield is rotated to the closed position. The housing 42 further includes a locking element 52 to further ensure the needle shield cannot be displaced from the closed position. The needle shield includes a pair of inwardly extending tabs 54 near its proximal end that ride over and then snap behind the locking element 52. While the shield is locked in the closed position by engaging both the cannula 38 and the locking element 52, either manner of locking would provide satisfactory performance. It should be understood that there are a variety of ways of protecting against needle sticks other than pivotable needle shields.

The needle assembly 28 and the syringe are constructed so that the needle assembly may be removably connected to the syringe tip 24. Forcing the hub towards the syringe tip will cause the frusto-conically shaped tip to engage the corresponding hub portion in a frictional interference fit which, normally, will require a certain amount of force for disengagement. Needle assembly hubs are commonly made of injection molded plastic while syringes are commonly made of injection molded plastic or glass. The frusto-conically shaped interior of the hub passageway and the frusto-conically-shaped exterior of the syringe tip are normally smooth, as manufactured. The frictional interference fit between the syringe tip and the hub accordingly may not be optimal. The presence of liquid may reduce the strength of the fit between the hub and the syringe tip because it may act as a lubricant film.

As discussed above, various solutions have been proposed for improving the retention of needle assemblies and syringes. The instant invention provides substantial improvements over previous approaches.

In accordance with a first and preferred embodiment of the invention, the interior surface of the needle hub 34 includes a portion that is comprised of an elastomeric material. The elastomeric material is preferably one that is compatible with the fluids ordinarily found in biomedical devices. Elastomers have properties that allow them to be stretched or otherwise deformed, yet return to their original positions. Materials believed to be suitable for incorporation within the hub include natural rubber and thermoplastic elastomers such as Santoprene rubber. The latter is an elastomeric alloy made by Advanced Elastomer Systems, and is used in the preferred embodiment described below.

Figure 9:
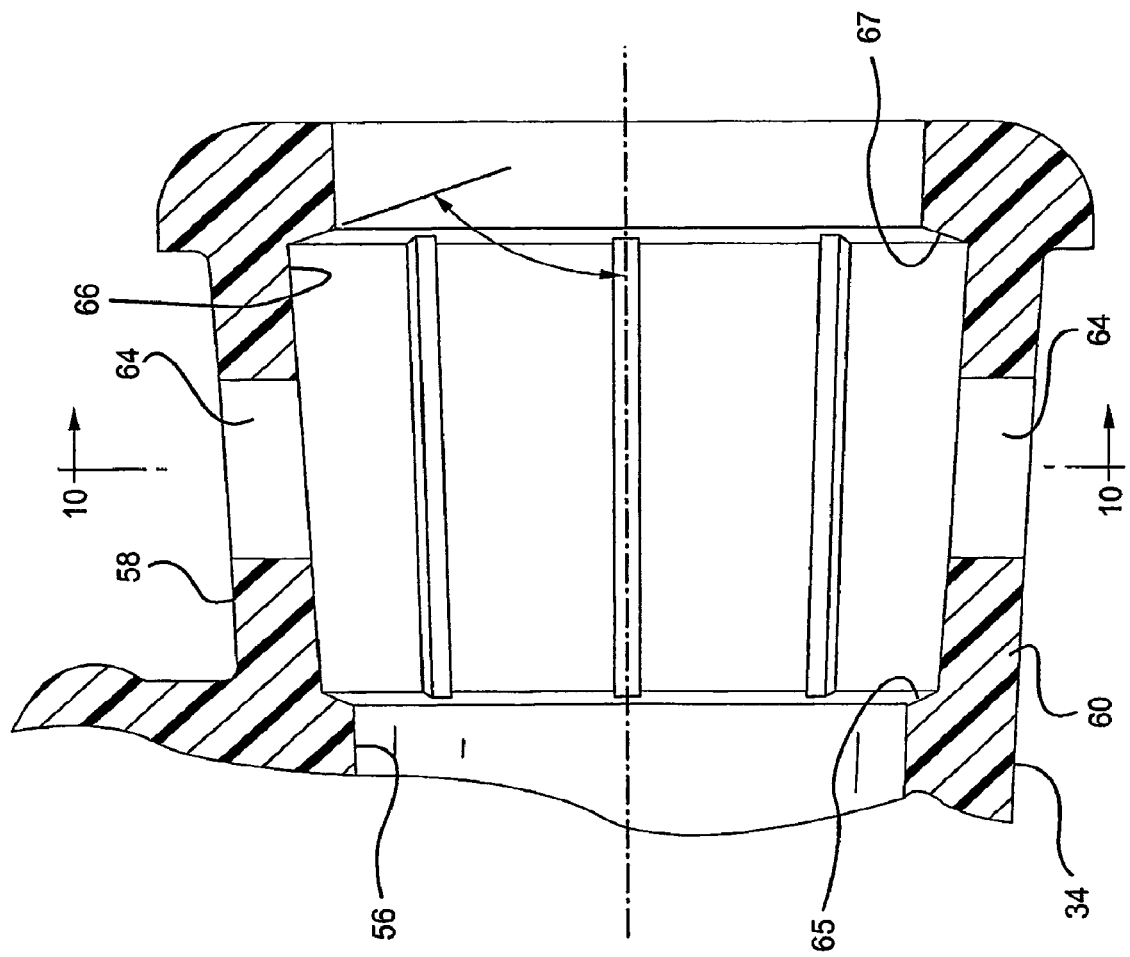
FIG. 9 is an enlarged cross-sectional view showing the proximal end of the needle hub of the needle assembly.

Referring again to the embodiment of FIGS. 1-10, the rigid or semi-rigid hub 34 is preferably made of plastic material such as polypropylene, polyethylene or combinations thereof. Hub 34 includes a tapered interior surface 56 and an outer surface 58. The proximal portion of the hub is constructed as a female luer fitting 60 and may include radially outwardly projecting wings 62. The wings allow the hub to be coupled to an internally threaded receptacle concentric to a luer tip. One or more channels 64 (as shown in FIG. 9) extend radially through the hub. Two such channels are provided in the first disclosed embodiment of the invention. A generally annular recess 66 is provided in the interior surface of the hub. The annular recess is bounded by a wall of the body of the female luer fitting, as best shown in FIG. 9. Each channel extends between the interior surface of the hub, where it adjoins the recess, and the exterior hub surface. The channels 64 are diametrically opposite from each other in this embodiment, one extending through the top of the fitting and the other through the bottom. They may alternatively extend through opposite sides of the fitting or elsewhere. One or more channels can be employed.

A soft, resilient member 68 is secured to the relatively rigid body of the female luer fitting 60. The soft, resilient member will deflect in response to physical pressure, such as the pressure exerted by a male luer fitting, and will tend to return to its original shape following deformation. As discussed hereafter, this member and the hub 34 are preferably manufactured using a two-shot molding process. Such a process requires the use of compatible materials. In this preferred embodiment, the relatively soft, resilient material is SANTOPRENE rubber, which is a synthetic rubber. SANTOPRENE Rubber 171-55 and 281-55 are two thermoplastic elastomers that would be suitable for use in forming the soft, resilient member 68. Both have a durometer hardness (A Scale (5 sec)) of 55 under test method ASTM D2240. The hub 34 is preferably made from a thermoplastic such as polypropylene, which is harder than the SANTOPRENE rubber. When used in the manufacture of products such as syringes and needle hubs, polypropylene is generally considered to be a semi-rigid material. The soft, resilient member 68 is secured to the body of the polypropylene female luer fitting 60 through the use of the two-shot molding process. As the member 68 has portions extending into the recess 66 and channels 64, it is mechanically coupled to the female luer fitting 60. These elements may also be bonded together as a result of the molding process.

The passageway 36 extending through the needle hub includes a generally frusto-conical portion in the area of the female luer fitting. In the embodiment of FIGS. 1-10, this portion of the passageway is bounded by the frusto-conical surface of the soft, resilient member as well as the harder inner surface 56 of the hub. While the entire inner surface of the female luer fitting could be comprised of a relatively soft, resilient member, this is not preferred. It is instead preferred that a male luer tip, when coupled to the hub, engage both the relatively soft, resilient member 68 as well as the relatively harder surface of the hub. The harder surface is engaged towards the distal end of the female luer fitting 60. In this preferred embodiment, the diameter of the passageway 36 is slightly smaller where it is bounded by the soft, resilient member than where it is bounded by the inner surface 56 of the hub. While the diameter of the passageway generally decreases in the direction of the distal end of the hub 34, the soft, resilient member 68 projects inwardly with respect to the inner surface 56, as shown in FIG. 3, such that it will frictionally engage a male luer member once positioned in the passageway. The soft, resilient member will also preferably be compressed slightly by the male luer member. The extent to which the soft, resilient member 68 projects inwardly with respect to the inner surface 56 may be determined by the desired coupling force between the male and female luer fittings. The user will preferably notice little or no appreciable difference in connecting the needle assembly 28 to the syringe from conventional designs even though the removal force is greater than in such designs.

In a preferred embodiment of the invention, the soft, resilient member extends about 0.076 mm (0.003 inch) inwardly of the inner surface 56. Its inner diameter is accordingly about 0.152 mm (0.006 inch) less than the inner diameter of the inner surface 56. The inner surface of the soft, resilient member 68 is tapered in the direction of the distal end of the hub at substantially the same angle as the inner surface 56 of the female luer fitting 60 in the embodiment of FIGS. 1-10. A generally frusto-conical passageway is accordingly provided within the female luer fitting, one portion of which is bounded by the soft, resilient member that will enhance the frictional retention of a male luer fitting. It will be appreciated that the areas of soft, resilient material and rigid or semi-rigid hub material bounding the passageway through the female luer fitting may be different from the embodiment of FIGS. 1-10. As discussed above, the passageway is preferably constructed such that the male luer fitting engages a combination of relatively soft, resilient material and the harder hub material. The male luer fitting is most likely comprised of a rigid or semi-rigid material such as polypropylene.

Figure 10:
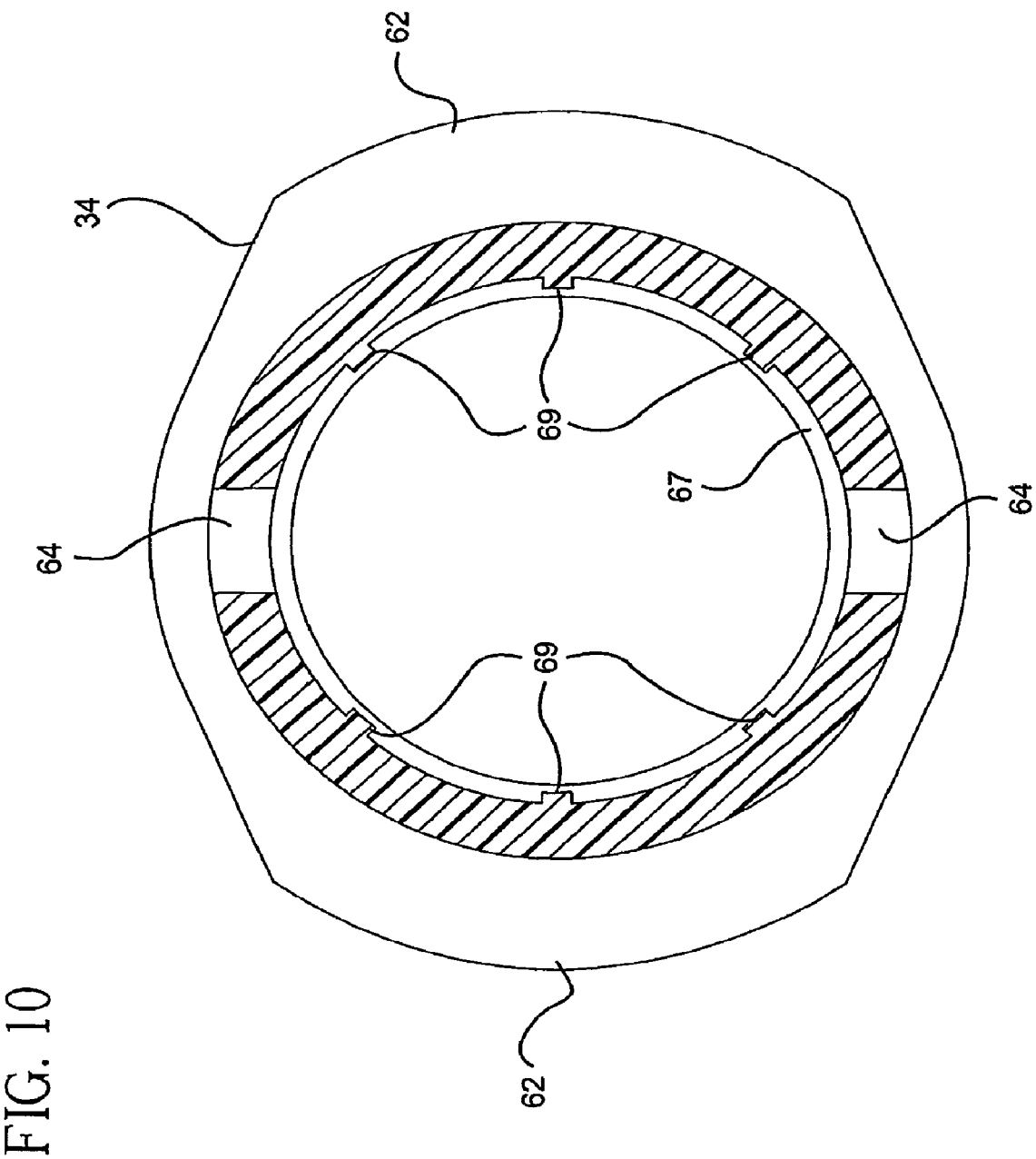
FIG. 10 is a cross-sectional view thereof taken along line 10-10 of FIG. 9.

FIGS. 9 and 10 provide substantially enlarged views of the body of the female luer fitting. The generally annular recess 66 is bounded by a distal shoulder 65 and a proximal shoulder 67. The shoulder 67 at the proximal end of the recess is preferably formed in such a manner that it causes the soft, resilient member 68 to exert an increased radial force on the male luer tip as one attempts to withdraw the male luer tip from the passageway 36. In other words, the retention force exerted on the male luer tip increases as one attempts to move it in the proximal direction until a point at which the tip is released. Referring to FIG. 9, the recess 66 has a depth of about 0.254 mm (0.010 inch). The shoulder 67 at the proximal end of the recess forms an angle with the longitudinal axis of the hub 34 which is desirably between about fifty-six to sixty degrees, and preferably about fifty-eight degrees.

It is important for the soft, resilient member 68 to remain coupled to the female luer fitting 60 and resist displacements during use. As discussed above, this member is subjected to force as the male luer tip is inserted, and would also have forces exerted thereon of the male luer tip is withdrawn. It is also possible for the soft, resilient member 68 to be subjected to torsional forces if the male luer tip is twisted or rotated with respect to the female luer fitting. Such twisting may occur in an attempt to uncouple male and female fittings. It will occur if the hub 34 is threadably coupled to a luer lock assembly as described above. The channels 64 in the hub and the recess 66 mechanically couple the soft, resilient member 68 and the female luer fitting 60. The diameter of the channels are slightly greater near the exterior surface of the female luer fitting 60 than where they adjoin the recess 66 in this preferred embodiment. One or more longitudinal ribs 69 extend between the proximal and distal shoulders 65, 67. As shown in FIG. 10, the depth of the recess exceeds the height of the ribs 69.

The needle assembly 28 may be provided to the user as shown in FIG. 1 with a removable sheath 70 protecting cannula 38 when the shield 46 is in the open position. The assembly is coupled to a syringe by urging the female luer fitting 60 over the male luer fitting (tip 24) of the syringe barrel. Once the needle shield 46 is pivoted back and the sheath 70 is removed by disengaging it from the open distal end of housing 42 of hub 34, the syringe is ready for use. FIG. 4 shows a syringe having an attached needle assembly 28 with the shield fully rotated back and the sheath removed. The shield may be moved to the closed position shown in FIGS. 5-7 following use. It is locked in the closed position by the projections 50 that trap the cannula 38 and the tabs 54 that adjoin the locking element 52 on the housing 42. It is to be appreciated that the present invention is applicable to assemblies having female luer fittings that may or may not be incorporated as parts of needle assemblies. Moreover, the needle assemblies may include shields different from the shield disclosed herein or may be shieldless.

FIG. 6 shows the needle assembly 28 as coupled to a syringe having a tip 24 including a standard luer taper. The soft, resilient member 68 is compressed between the semi-rigid body of the female luer fitting 60 and the tip 24. It is important that the recess 66 is large enough to accommodate the compressed member so that it is substantially flush with the inner surface 56. In addition, the distal end portion of the tip 24 contacts the relatively hard inner surface 56 of the hub, preferably forming a fluid-tight seal therewith. Although the needle assembly can be uncoupled from the syringe, more effort is required than if both the tip 24 and the female luer fitting were both made entirely of a rigid or semi-rigid material. The chance of accidental disengagement is accordingly reduced. The laterally extending wings 62 at the proximal end of the needle assembly provide versatility in that they can be used to threadably couple the needle assembly to a syringe having a threaded collar (not shown). By causing the engagement of first the soft, resilient member 68 and then the relatively hard hub material bounding the passageway 36 with the tip 24, the user is likely to experience two different tactile sensations, the first when contact is made with the soft, resilient member 68 and the second when the tip engages the hub material. The engagement of the tip and hub material, both of which are preferably made from a plastic material such as polypropylene, produces a reliable fluid seal. While a seal may also be provided by the soft, resilient member 68, this member is primarily used for its frictional properties in the preferred embodiment disclosed herein.

Figure 11:
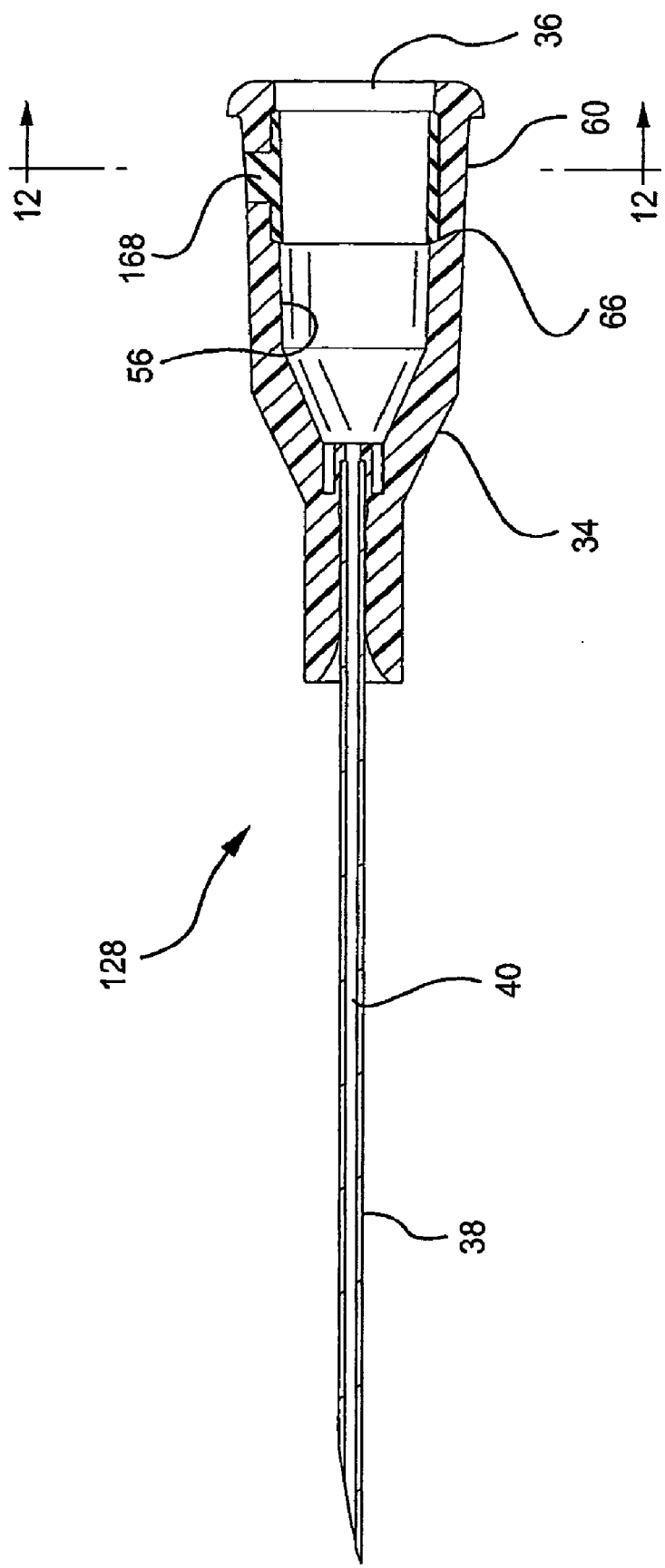
FIG. 11 is a cross-sectional view showing a second embodiment of a needle assembly according to the invention.
Figure 12:
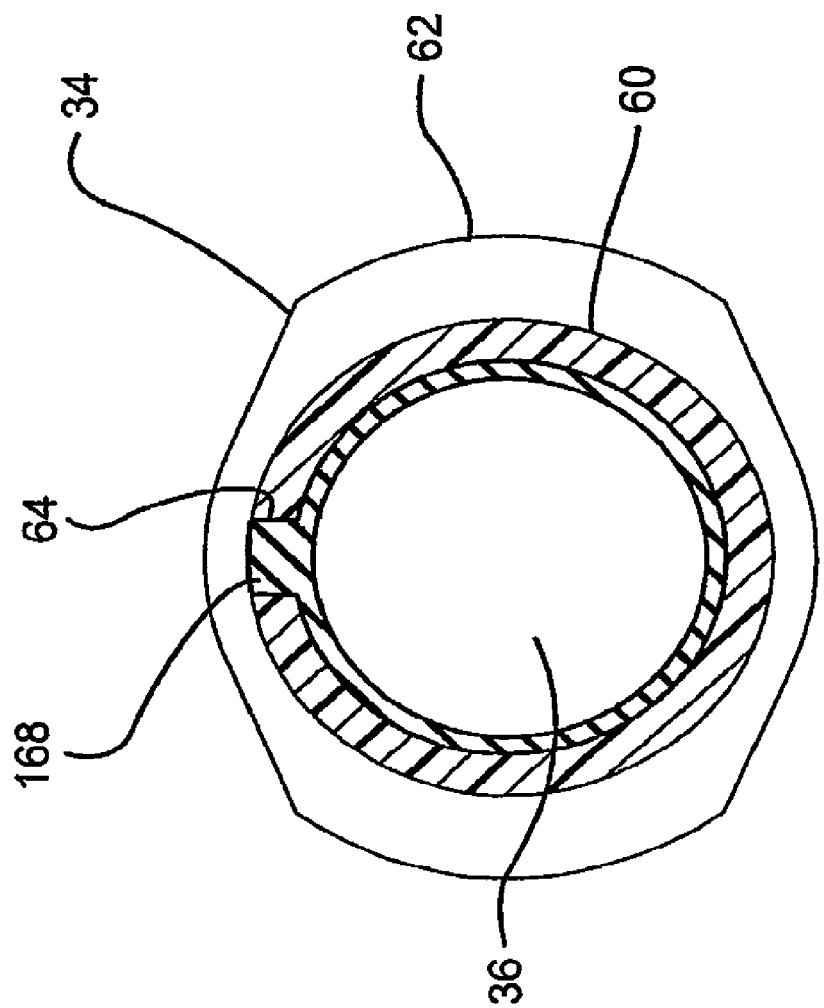
FIG. 12 is a cross-sectional view thereof taken along line 12-12 of FIG. 11.

FIGS. 11 and 12 disclose a needle assembly 128 similar to that described with respect to FIGS. 1-10. The same reference numerals are accordingly employed to designate elements similar to those found in FIGS. 1-10. In this embodiment, only one channel 64 extends through the hub 34, as opposed to the two channels in the previous embodiment. The soft, resilient member 168 accordingly extends only through the one channel. It will be appreciated that various number of channels can be provided in the hub for retaining the soft, resilient member. The recess in the inner surface of the female luer fitting includes a proximally angled shoulder defining its proximal end, similar to the shoulder 67 described above. The recess further extends both distally and proximally beyond the channel 64. The soft, resilient member 168 has an inner surface adjoining and possibly bonded to the body of the female luer fitting 60. It also extends both distally and proximally beyond the channel.

The manufacture of needle assemblies 28, 128 is preferably accomplished by selecting compatible materials, such as polypropylene and SANTOPRENE rubber, and molding them in a two-shot molding process. Various two-shot molding techniques are known in the molding art. In accordance with one such technique applied to the present invention, the polypropylene is injected, and the SANTOPRENE rubber is injected over the polypropylene. This is preferably accomplished in the same mold through the use of two injecting units. The polypropylene hub portion is first molded and allowed to cool for a short time. The SANTOPRENE rubber is injection molded over it using the second of the two injecting units. The channel(s) and recess provided in the hub portion provide a mechanical connection between the SANTOPRENE rubber and polypropylene components. A bond between these components may also be formed in this molding process. The resulting product is a substantially rigid hub having selected interior portions that are relatively soft and provide excellent frictional properties.

Figure 13:
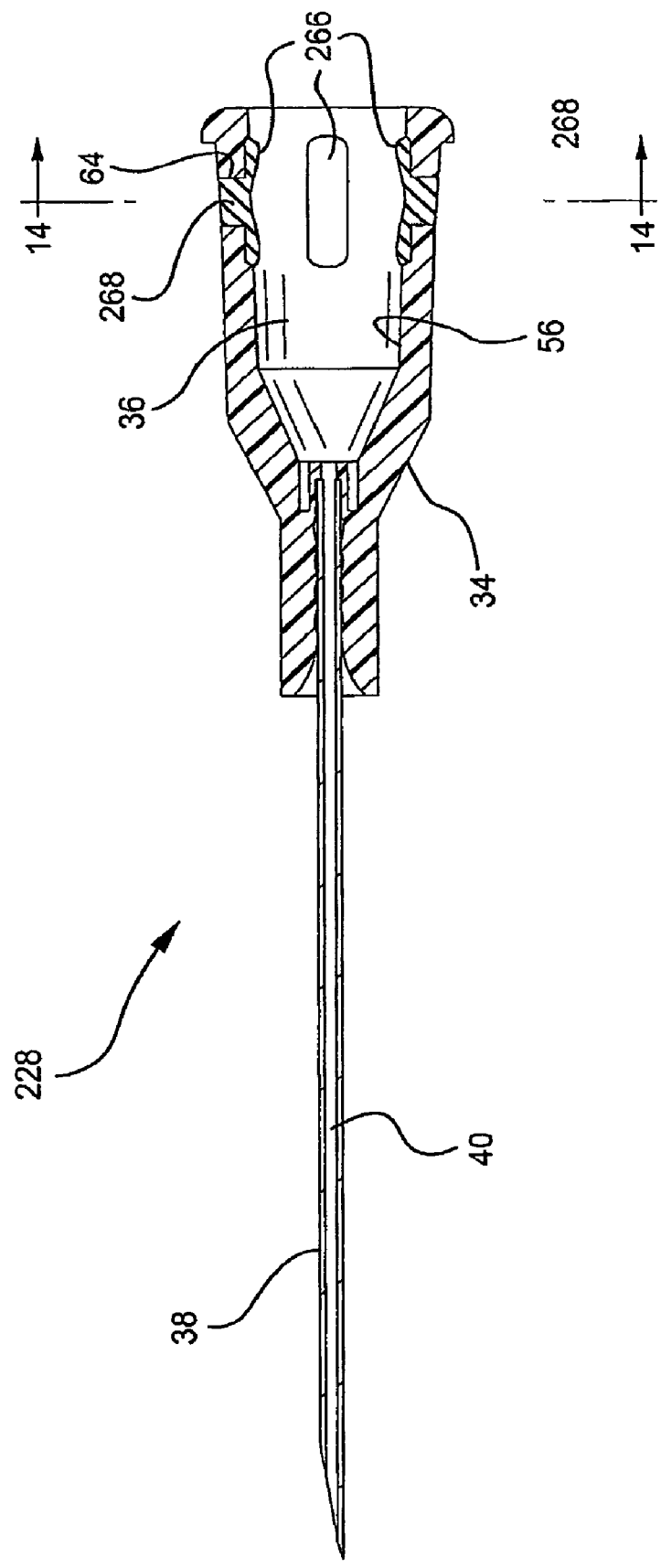
FIG. 13 is a cross-sectional view showing a needle assembly according to a third embodiment of the invention.
Figure 14:
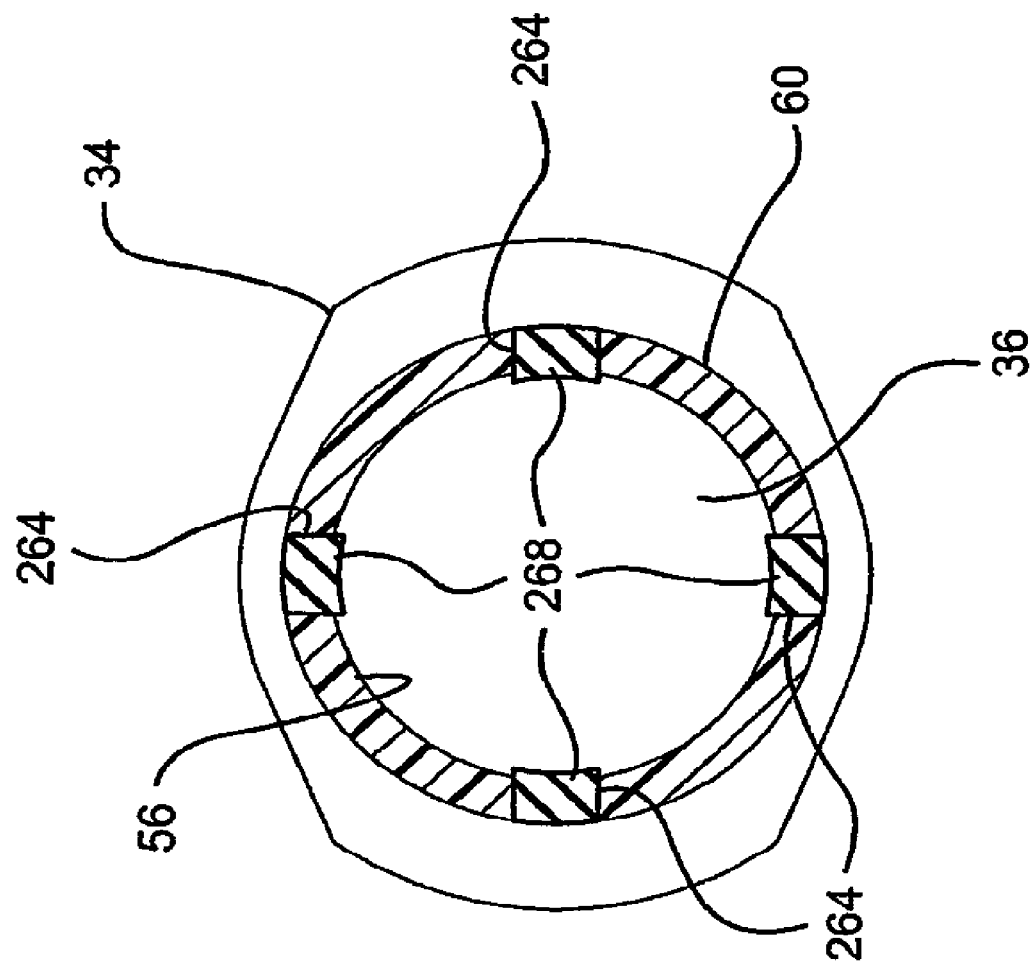
FIG. 14 is a cross-sectional view thereof taken along line 14-14 of FIG. 13.

The needle assembly 228 of FIGS. 13-14 includes a hub 34 that includes four separate recesses 266 rather than the generally annular recess 66 found in the embodiments of FIGS. 1-12. Four channels 64 extend through the female luer fitting 60 and respectively adjoin the recesses 266. Four soft, resilient members 268 are positioned in the channels and recesses. Each such member includes a wavy inner surface bounding the passageway 36. These members are coupled to the hub 34 using the molding techniques described above. The resilient members can also be secured to the hub by an adhesive.

Figure 15:
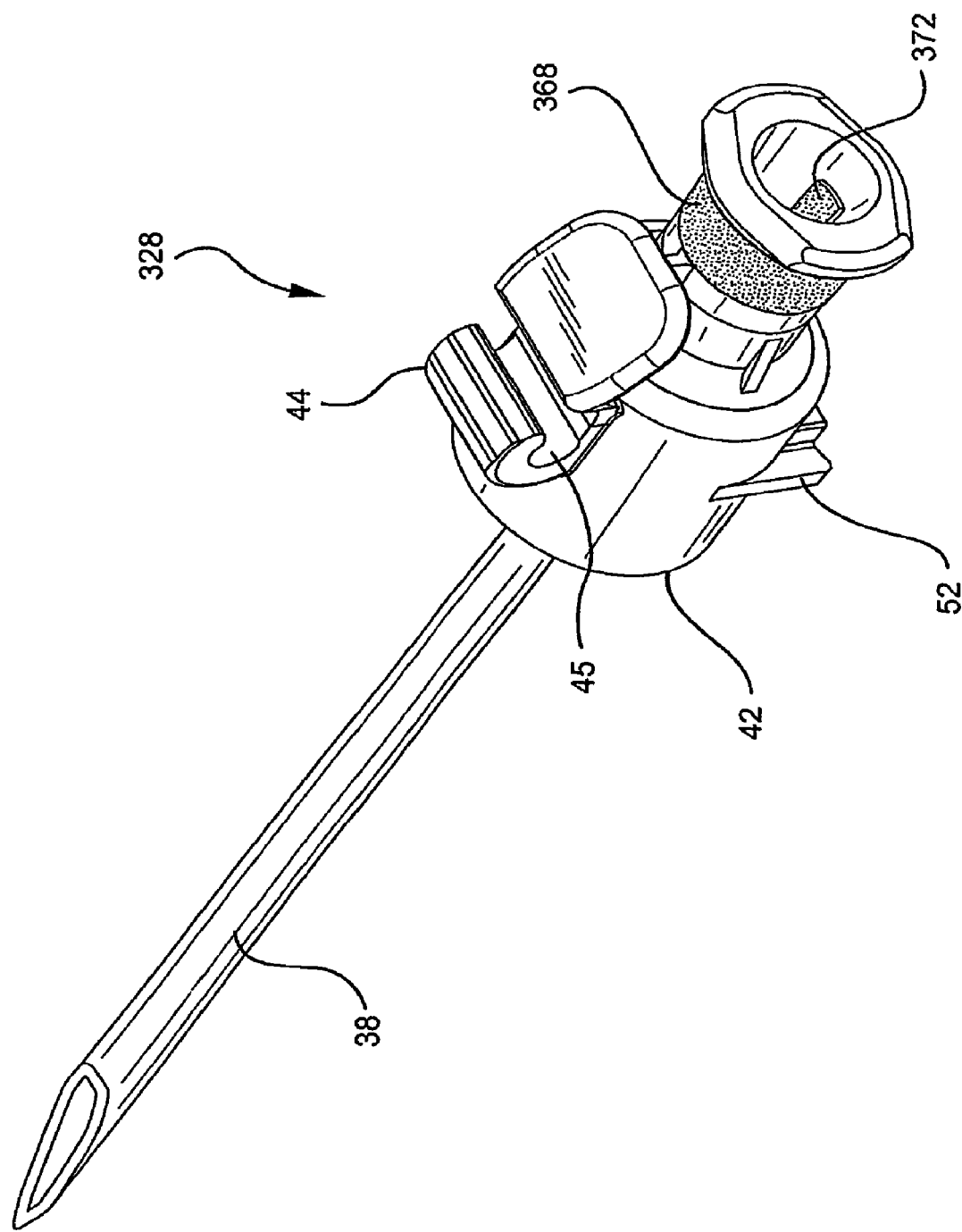
FIG. 15 is a top perspective view showing a needle assembly according to a fourth embodiment of the invention.
Figure 16:
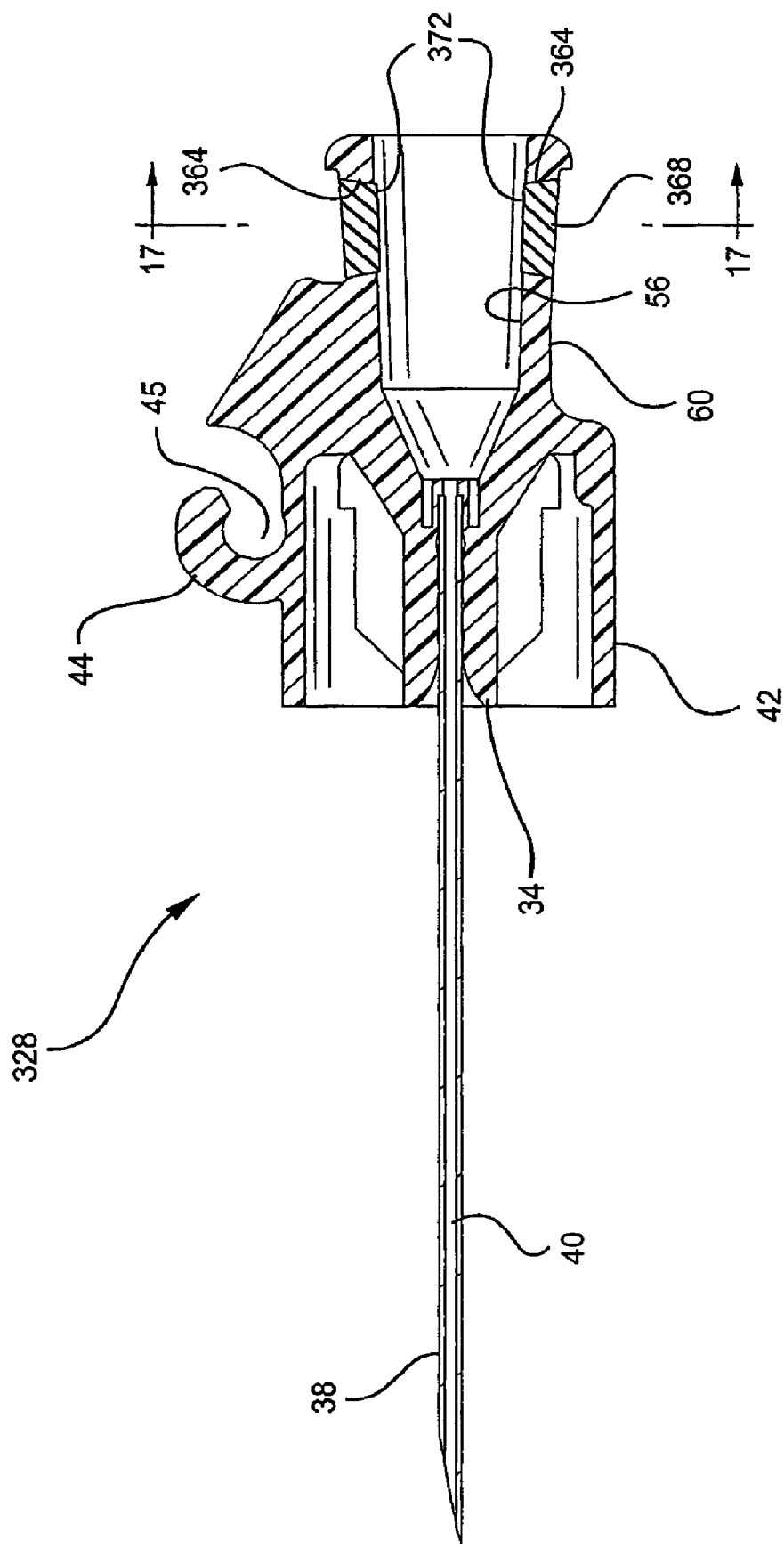
FIG. 16 is a cross-sectional view of the needle assembly of FIG. 15.
Figure 17:
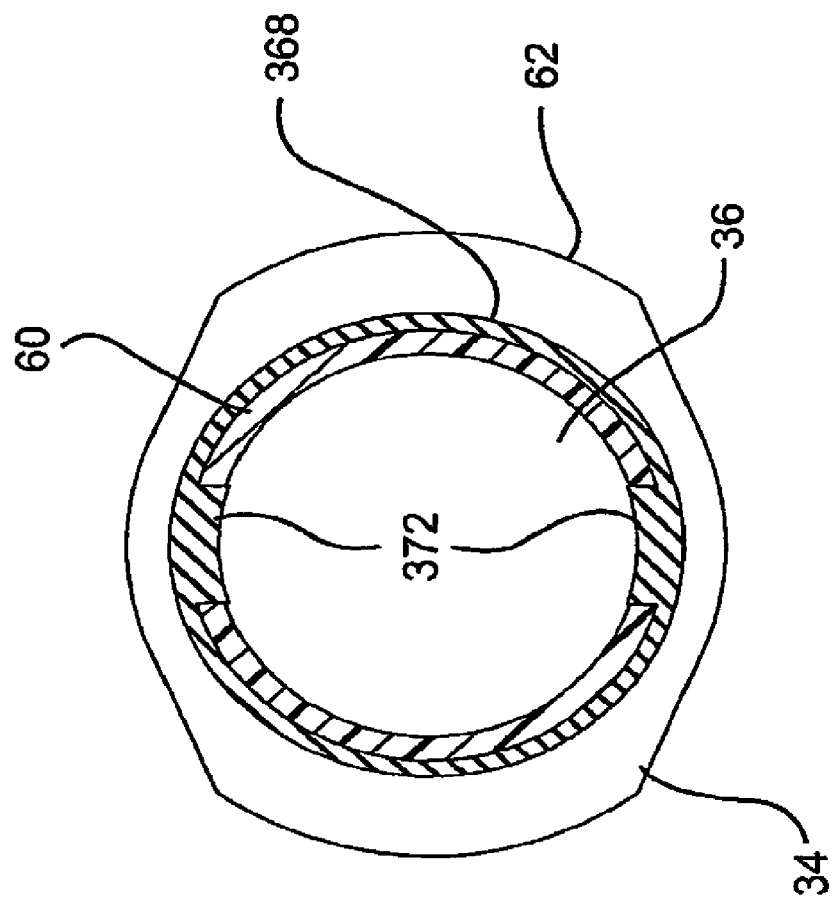
FIG. 17 is a cross-sectional view thereof taken along line 17-17 of FIG. 16.

FIGS. 15-17 disclose a fourth embodiment of the invention. In this embodiment, the needle assembly 328 includes a pair of opposing channels 364. The soft, resilient member 368 includes a generally annular or frustoconical exterior portion 370 that adjoins the exterior surface of the body of the female luer fitting 60. Two radially inwardly extending portions 372 of the soft, resilient member 368 extend through the channels 364 and into the passageway 36 to provide frictional engagement surfaces for retention of a male luer fitting. As in the previous embodiments, the inwardly extending portions 372 of the soft, resilient member 368 are displaced radially outwardly by the male luer fitting (not shown) such that they become substantially flush with the inner surface 56 of the female luer fitting. In addition, the male luer fitting engages and preferably forms a fluid tight seal with the inner surface 56 distal to the soft, resilient member 368. As in the embodiment of FIGS. 1-12, it is preferred that the hub and resilient members be formed by a two-shot molding process. However, resilient member 368 may be made as a separate member and slipped over the hub in to the position illustrated with or without an adhesive to hold the resilient member to the hub.

Figure 18:
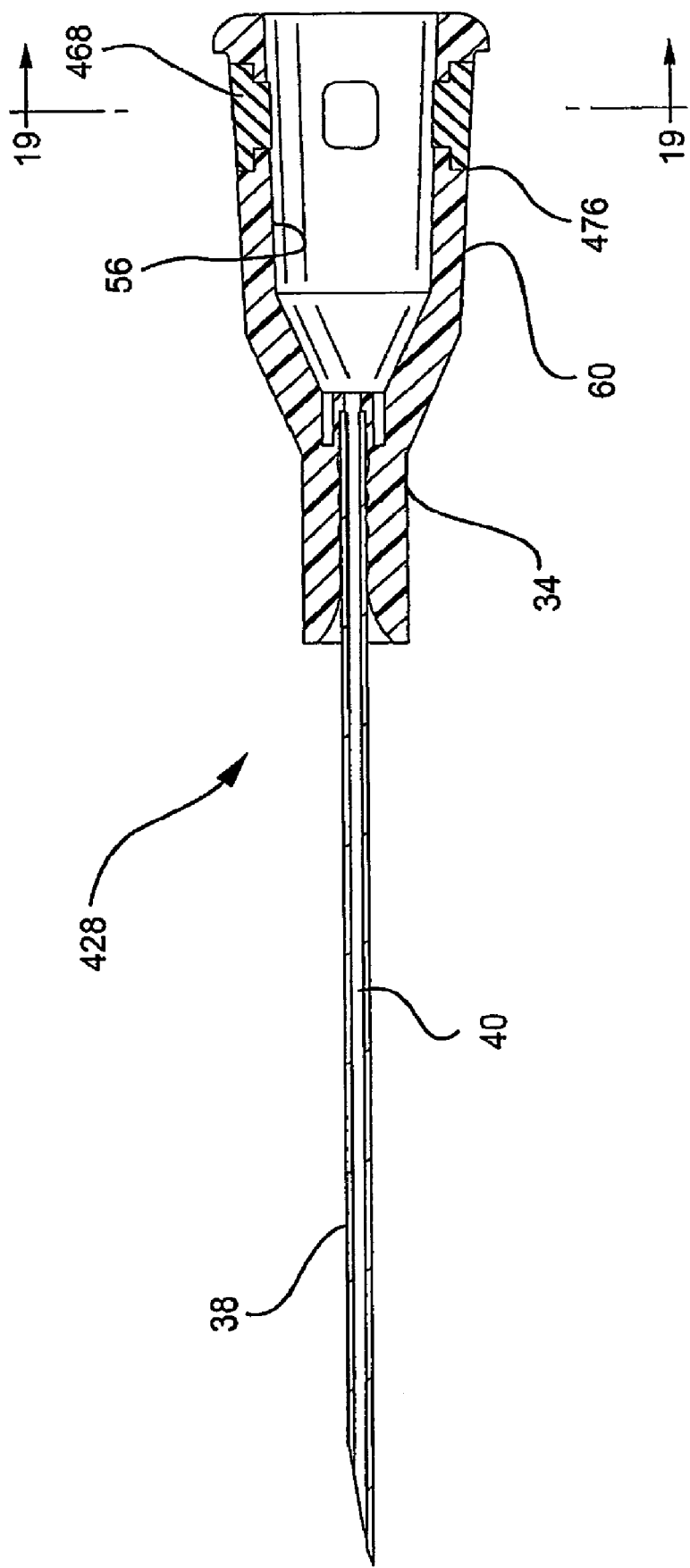
FIG. 18 is a cross-sectional view showing a needle assembly according to a fifth embodiment of the invention.
Figure 19:
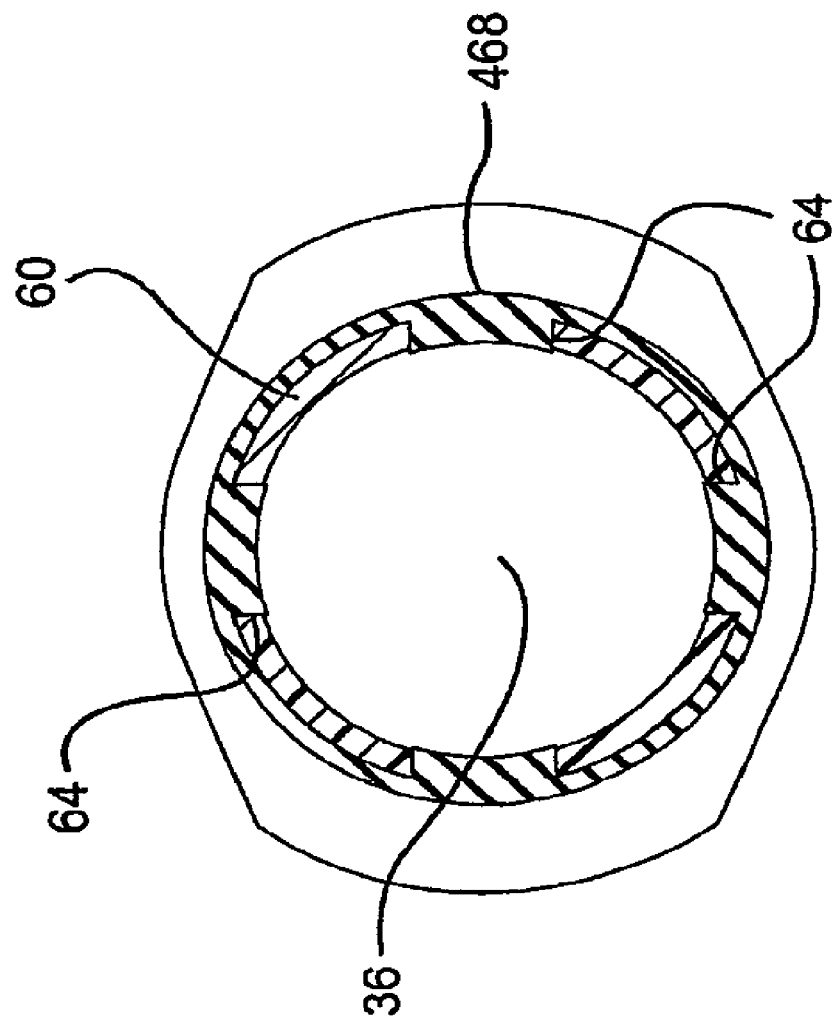
FIG. 19 is a cross-sectional view thereof taken along line 19-19 of FIG. 18.

FIGS. 18-19 show a fifth embodiment of the invention. It is similar to the embodiment of FIGS. 15-17 in that the exterior surface of the female luer fitting 60 is defined in part by the exterior surface of a soft, resilient member 468. Four channels 64 extend through the female luer fitting. Portions of the soft, resilient member 468 extend through the channels and into the passageway 36. Unlike the first three embodiments, where the recesses 66 in the interior surface of the body of the female luer fitting extend beyond the channel openings, both distally and proximally, the recesses and channels 64 of this needle assembly 428 are coextensive. It is also similar to the fourth embodiment in this respect. The recesses accordingly have not been designated with separate reference numerals in either the fourth or fifth embodiments. In all of the embodiments, the recesses allow for the radial displacement of the soft, resilient member when a male luer fitting is within the passageway, allowing this member to become substantially flush with the inner surface 56 of the hub. In the embodiment of FIGS. 18-19, a generally annular recess 476 extends within the exterior surface of the female luer fitting. The channels 64 extend between the recess 476 and the inner surface 56 of the hub. Insertion of a male luer fitting into a passageway 36 causes the radial displacement of the portions of the soft, resilient member 468 that project into the passageway. The male luer fitting will be engaged by both the inwardly projecting portions of the soft, resilient member and the relatively hard inner surface 56 of the hub. It preferably forms a fluid tight seal with the inner surface of the hub distal to the area of engagement with the soft, resilient member 468.

Figure 20:
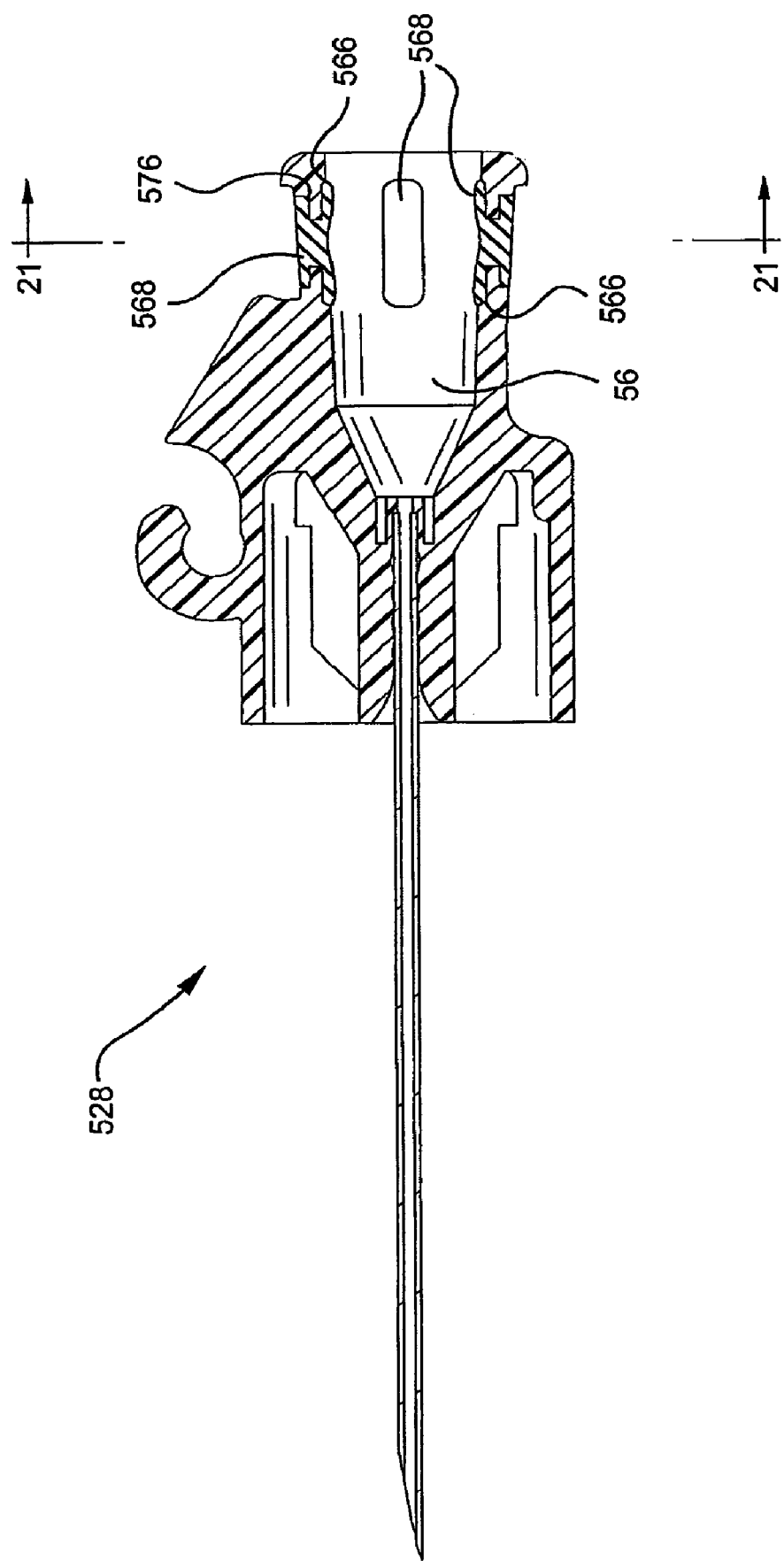
FIG. 20 is a cross-sectional view showing a needle assembly according to a sixth embodiment of the invention.
Figure 21:
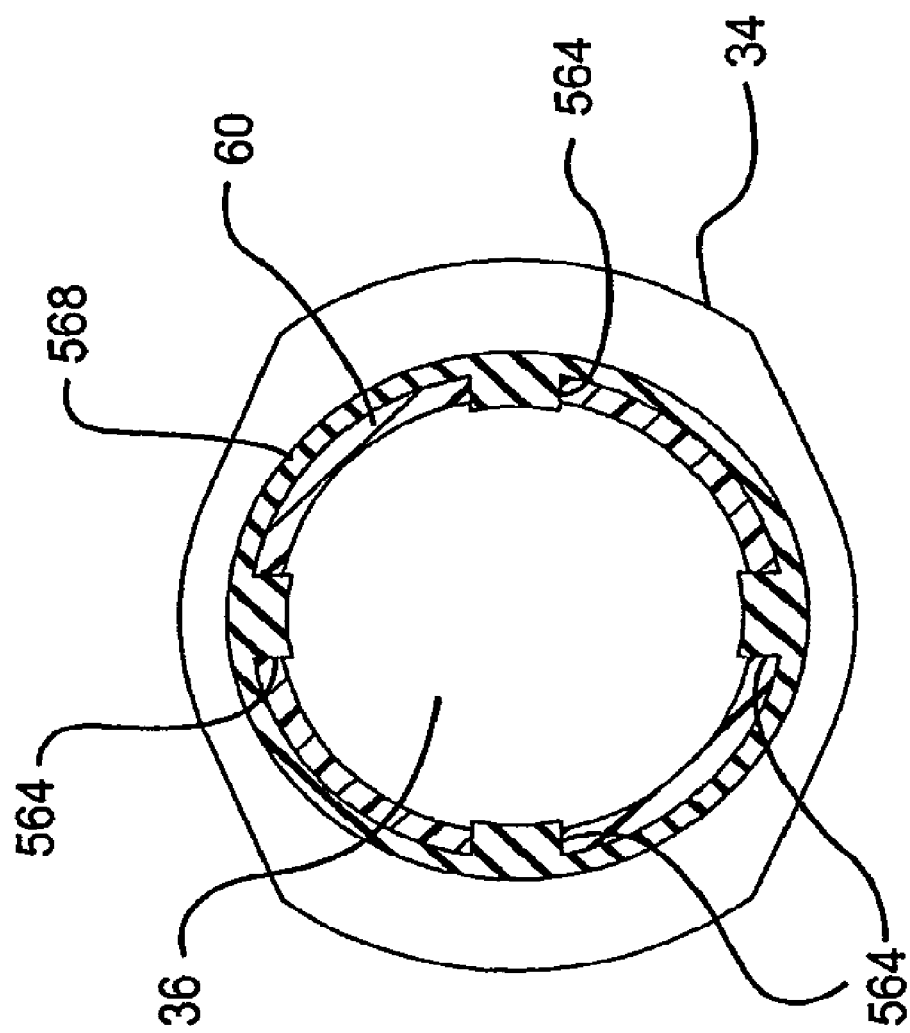
FIG. 21 is a cross-sectional view thereof taken along line 21-21 of FIG. 20.

FIGS. 20-21 show a needle assembly 528 according to a sixth embodiment of the invention. In this embodiment, recesses 566 and 576 extending beyond the inner and outer openings of the channels 564 are provided in the inner surface 56 and the outer surface of the hub, respectively. The inner recesses 566 include generally rectangular outlines while the outer recess is generally annular or frustoconical. It will be appreciated that the inner recesses 566 could be formed as a generally annular recess as well, similar to that of the first described embodiment. The inner surfaces of the portions of the soft, resilient member 568 are shown as wavey. They could, however, generally conform to the shape of the inner surface 56 of the hub in the area of the female luer fitting 60, which is frustoconical. As in the previously described embodiments, a male luer fitting positioned in the passageway 36 will engage both the soft, resilient member 568 and the relatively hard inner surface 56 of the hub. It will displace the portions of the soft, resilient member 568 that extend in the passageway 36 so that they are substantially flush with the inner surface 56.

Figure 22:
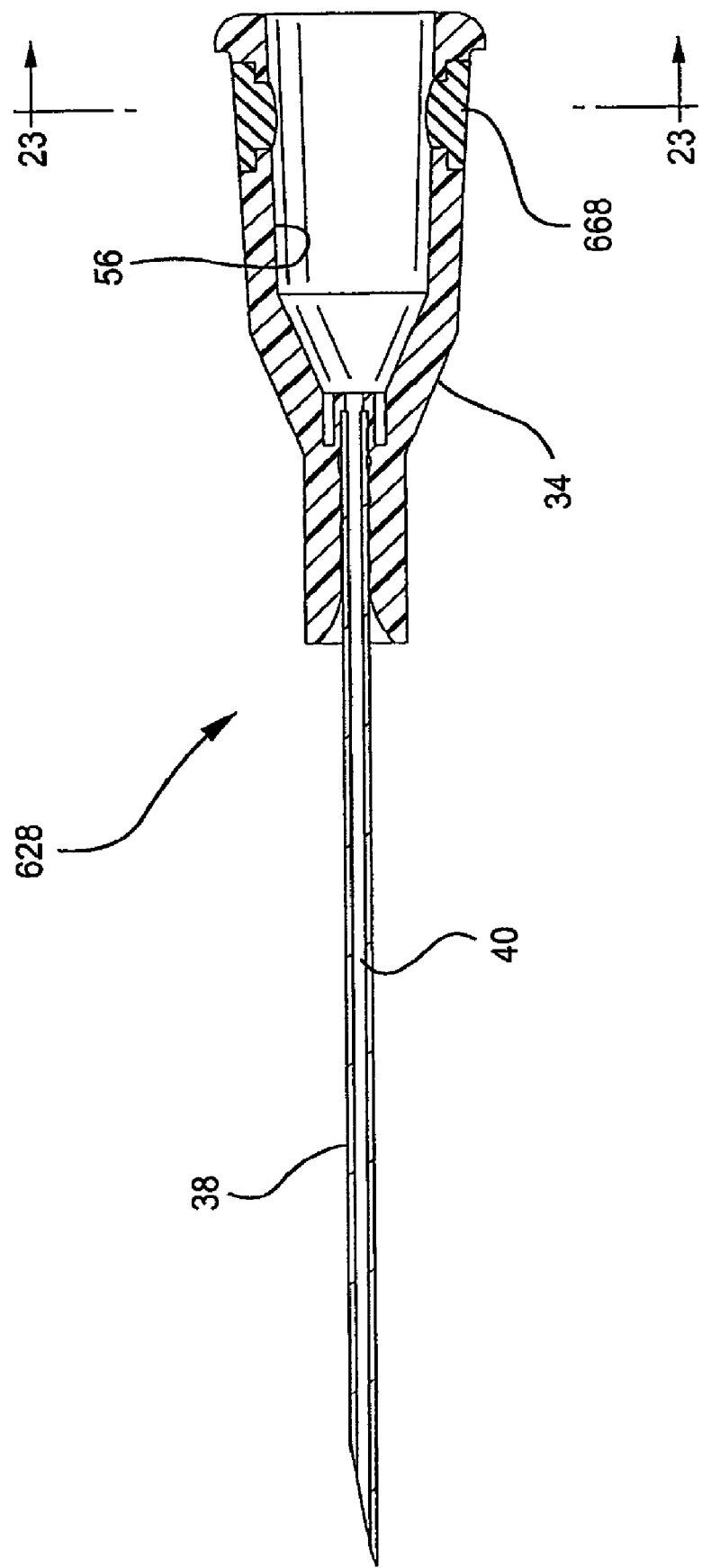
FIG. 22 is a cross-sectional view showing a needle assembly according to a seventh embodiment of the invention.
Figure 23:
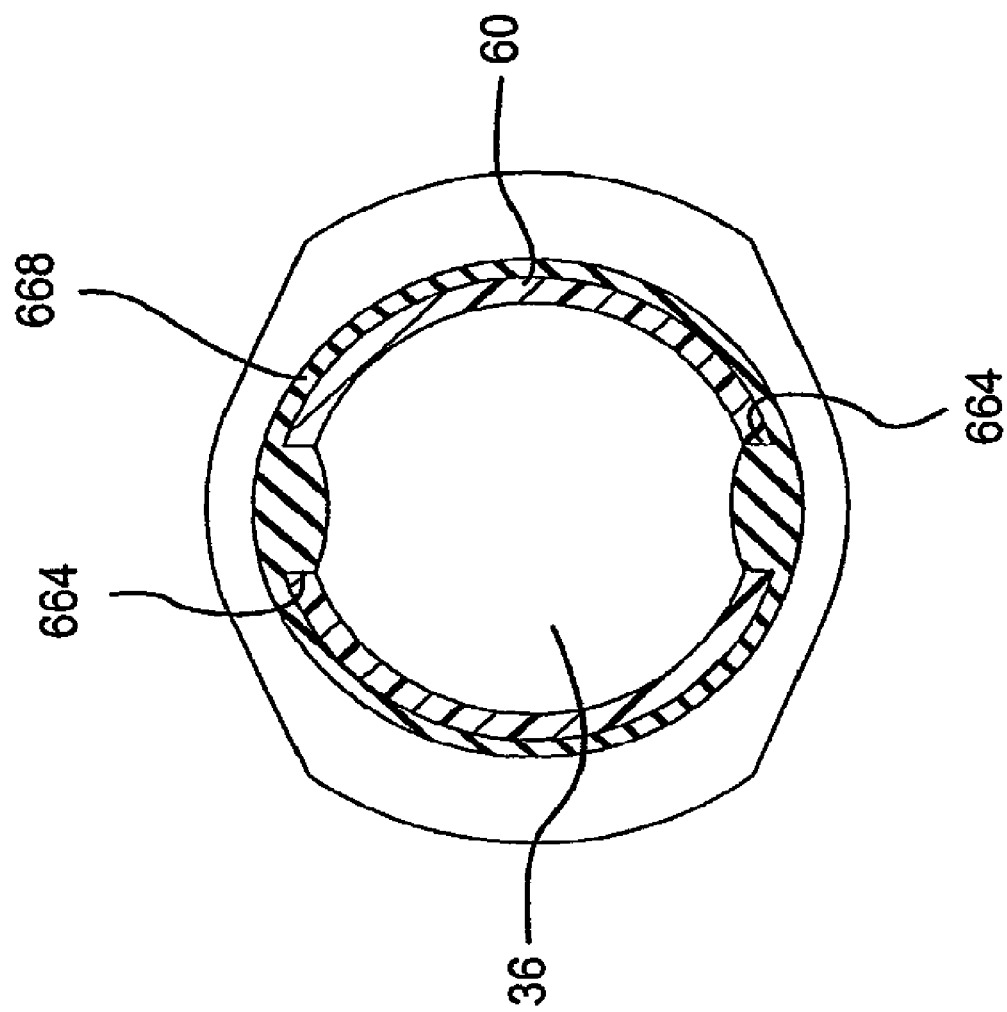
FIG. 23 is a cross-sectional view thereof taken along line 23-23 of FIG. 22.
Figure 24:
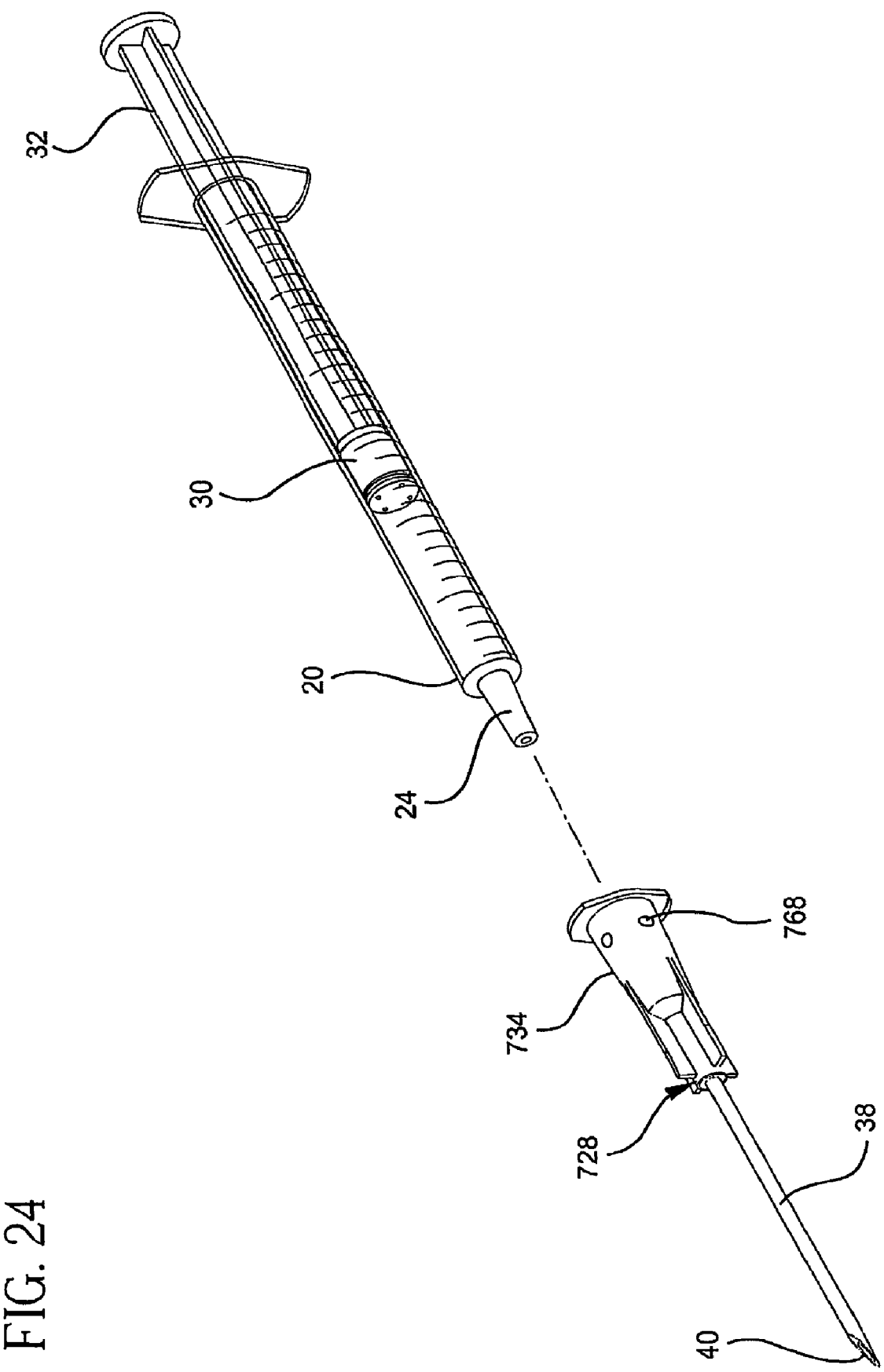
FIG. 24 is an exploded, perspective view showing a syringe and needle assembly according to an eighth embodiment of the invention.
Figure 25:
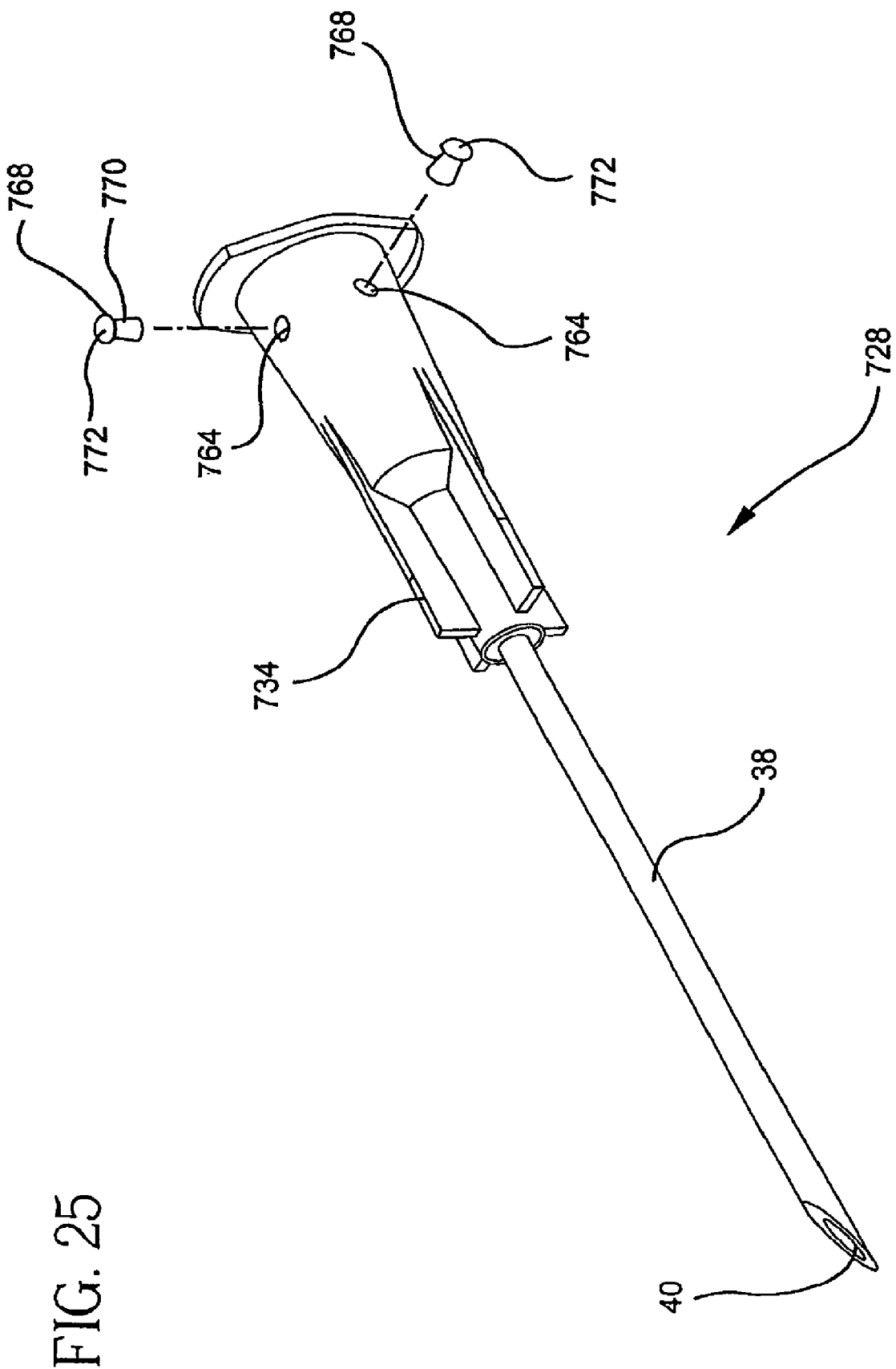
FIG. 25 is an exploded, perspective view showing a needle assembly of FIG. 24.
Figure 26:
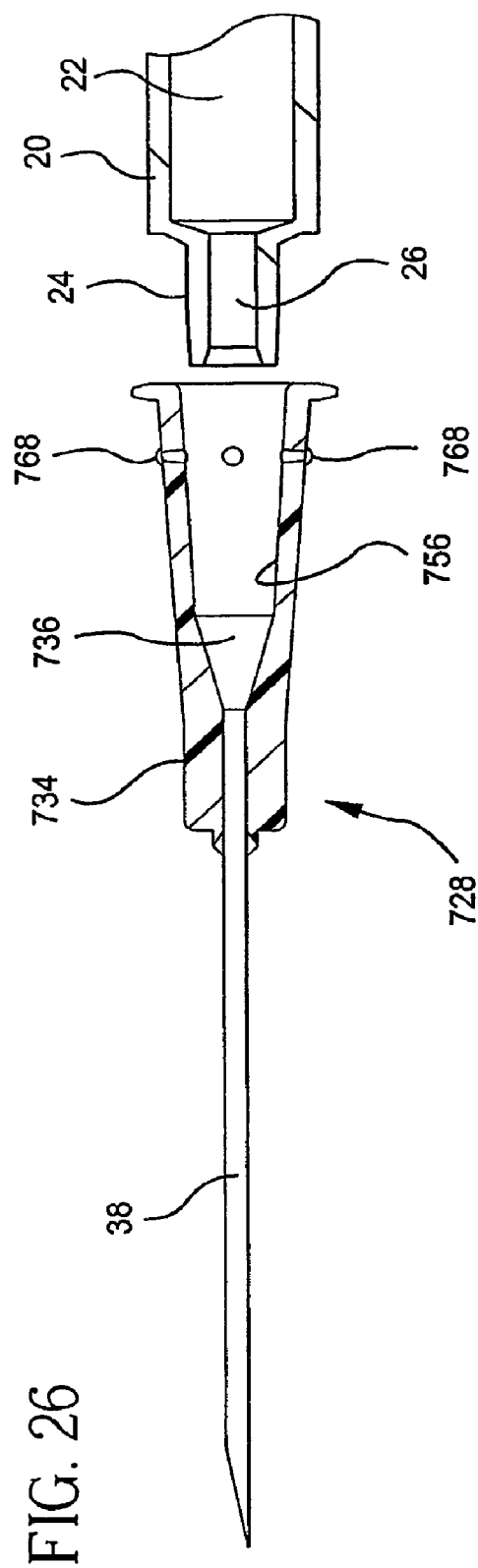
FIG. 26 is a cross-sectional view thereof showing the needle assembly prior to its coupling to the syringe.
Figure 27:
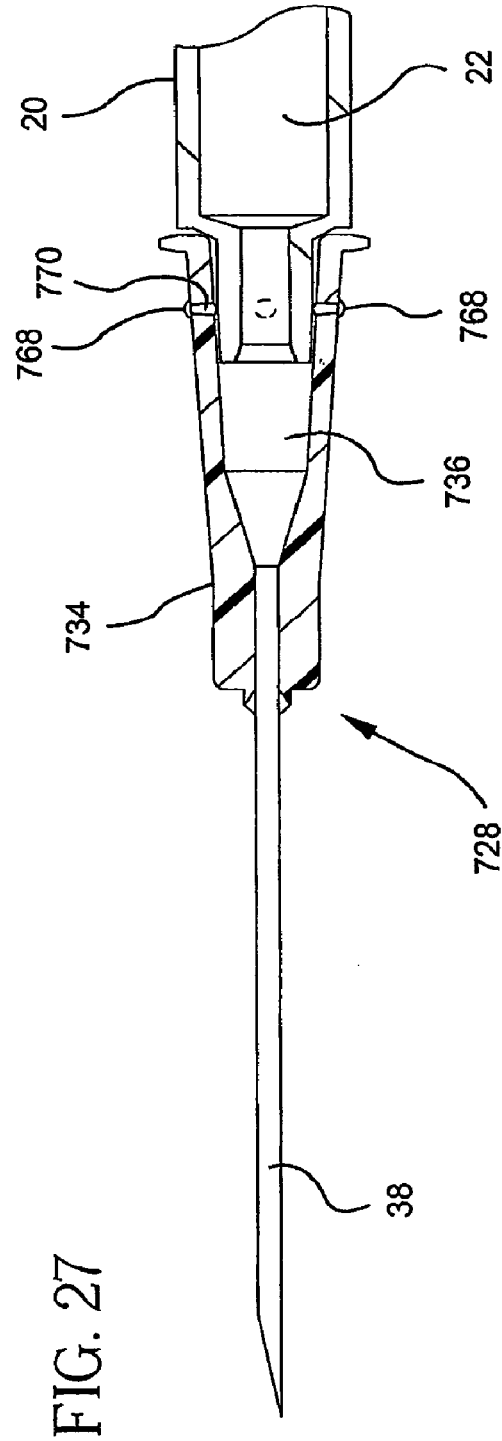
FIG. 27 is a cross-sectional view thereof showing the needle assembly coupled to the syringe.

A needle assembly 628 according to a seventh embodiment of the invention is shown in FIGS. 22-23. This embodiment is substantially the same as that shown in FIGS. 18-19, only the inner surfaces of the soft, resilient member 668 are generally convex. When compressed by a male luer fitting, the portion of the resilient member 668 projecting into the passageway will be displaced into the channel/recess 664 from which it extends.

An eighth embodiment of the invention is shown in FIGS. 24-27. In this embodiment, one or more elastomeric plugs 768 are coupled to the hub 734 of a needle assembly 728. The hub 734 includes one or more radially extending channels 764 extending between the inner and outer surfaces thereof. Each plug includes a shaft portion 770 that extends through a channel 764 and preferably an enlarged head portion 772 integral with the end of the shaft portion contacting the outer surface of the hub. As head portion is larger in diameter than the channel, the plug is restrained from falling into the hub. Channels 764 and shaft portions 770 are tapered to be larger at the inside surfaces of the hub than at the outside surface, to prevent plugs 768 from being pushed out of the channels when the hub engages a male luer fitting. The plug can be mechanically coupled to the hub or multi-shot molded with the hub with or without the head portions. If mechanically coupled, only the inner portion must be of elastomeric material. The remainder of the plug can be comprised of other materials, such as a rigid or semi-rigid plastic material. The plug or portion thereof adjoining the passage 736 should be non-reactive with the fluids that are likely to be delivered by the syringe or other medical device.

Figure 28:
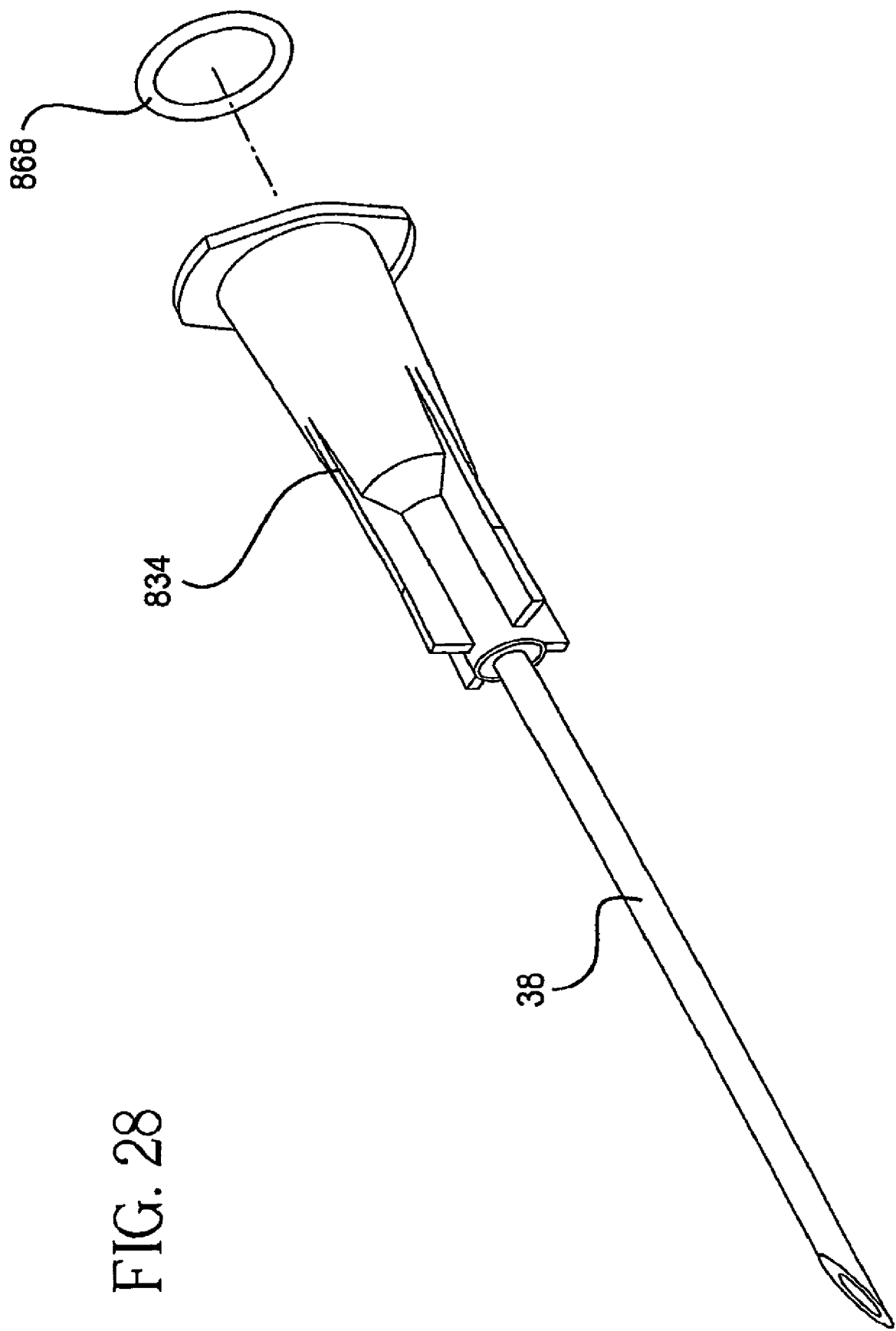
FIG. 28 is an exploded perspective view showing a needle assembly according to a ninth embodiment of the invention.

As shown in FIG. 28, the inner head portion 772 of the plug 768 deforms when the tip 24 of the syringe is inserted into the passageway 736 of the needle hub 734. The retention force between the needle hub 734 and tip 24 is accordingly superior to that provided by an interference fit between these parts in the absence of the plug. A substantially fluid-tight coupling of the needle hub and tip is also provided despite the presence of the elastomeric material. This is accomplished through the use of a relatively small, readily compressible head portion that, when compressed between the needle hub and tip, creates substantially no gaps of such size that would compromise the seal between these elements. It will be noted that a portion of the inner head portion 772 of the plug 768 overlies the frustoconical inner surface 756 of the hub 734. This is in contrast to the above-described embodiments where no portions of the soft, resilient members overlie this surface. It is preferable to have no portion of the soft, resilient member(s) directly on the inner hub surface, and to provide an area or areas within the inner hub surface for these member(s) to move when compressed by the male luer fitting. As discussed above, it is preferable that the inner surface of soft, resilient member becomes flush with the inner hub surface when a male luer fitting is within the passageway so that both the inner hub surface and the inner surface of the resilient member contact the male luer fitting to form a seal. If the resilient member is too large or the recess not adequate to accept the resilient member when it is compressed, or if resilient material is trapped between the surface of the hub and the outer surface of the male luer fitting, an effective seal will not form between the hub and the male luer fitting.

Figure 29:
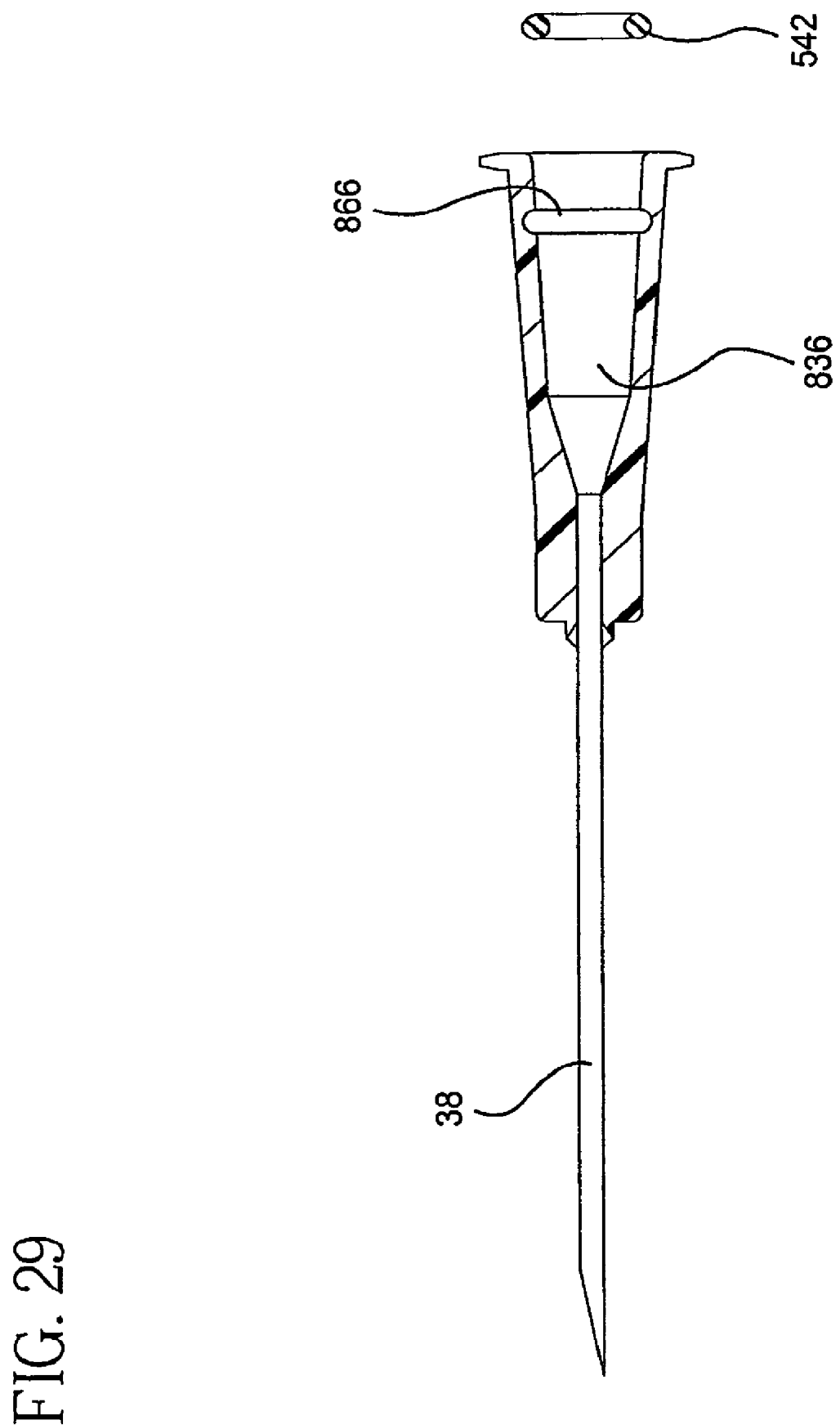
FIG. 29 is an exploded, cross-sectional view of the needle assembly of FIG. 28.

FIGS. 28-29 show a ninth embodiment of the invention wherein the inner surface of the needle hub 834 includes an annular groove 866 bordering the passageway 836. An elastomeric ring 868 is insertable into the passageway through the proximal opening in the needle hub, and can be positioned at least partially within the groove 866. Insertion of a luer tip within the passageway causes the ring 868 to be compressed, thereby enhancing retention as well as providing a fluid seal. The ring can be compressed sufficiently by a male luer fitting such that the ring is substantially contained by the groove. The groove should be large enough or have channels to allow ring 868 to be compressed until it is substantially flush with the inner surface of the hub.

It will be appreciated that the principles of the invention can be applied to female luer fittings used in connection with various medical devices, and that the devices shown and described herein are representative of the ways the invention can be employed.

What is claimed is:

1. An assembly for transferring fluid between a first medical device and a second medical device, comprising:
  a first medical device including a male luer fitting having a tapered exterior surface;
  a second medical device including a female luer fitting having a body including a tapered interior surface and a recess extending within said tapered interior surface, said female luer fitting being frictionally engaged to said male luer fitting such that said tapered exterior surface of said male luer fitting adjoins said tapered interior surface of said body of said female luer fitting;
  a passageway extending through said female luer fitting, said passageway being bounded by said tapered interior surface; and
  a soft, resilient member secured to said body and extending within said recess, said soft, resilient member being softer than said body of said female luer fitting and compressed by said exterior surface of said male luer fitting such that said soft, resilient member is substantially completely within said recess and substantially flush with said interior surface and in frictional engagement with said male luer fitting, wherein said body of said female luer fitting includes at least one channel extending from said recess to an outer surface thereof, said soft, resilient member extending into said channel.

2. The assembly of claim 1 wherein said male luer fitting frictionally engages said tapered interior surface of said body of said female luer fitting distal to said recess.

3. The assembly of claim 1 wherein said soft, resilient member is comprised of a thermoplastic elastomer.

4. The assembly of claim 1 wherein said soft, resilient member is mechanically coupled to said body of said female luer fitting.

5. The assembly of claim 4 wherein said soft, resilient member is coupled to said body of said female luer fitting through use of a two shot molding process.

6. The assembly of claim 5 wherein said soft, resilient member includes a generally frustoconical surface bounding said passageway.

7. The assembly of claim 1 wherein said body of said female luer fitting defines a proximally angled shoulder bordering a proximal end of said recess.

8. The assembly of claim 7, wherein said shoulder extends at an angle of between about 56 to 60 degrees with respect to a longitudinal axis of said passageway.

9. The assembly of claim 1 wherein said soft, resilient member includes a generally frustoconical surface bounding said passageway.

10. The assembly of claim 1 wherein said soft, resilient member adjoins an outer surface of said body of said female luer fitting.

11. The assembly of claim 1 wherein said first medical device is a syringe and said second medical device is a needle assembly.

* * * * *